US009031651B2

(12) United States Patent
Rockweiler et al.

(10) Patent No.: US 9,031,651 B2
(45) Date of Patent: May 12, 2015

(54) PHRENIC NERVE STIMULATION DETECTION

(71) Applicant: Cardiac Pacemakers, Inc., St. Paul, MN (US)

(72) Inventors: Holly Rockweiler, Minneapolis, MN (US); Sunipa Saha, Shoreview, MN (US); Yanting Dong, Lexington, KY (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/781,177

(22) Filed: Feb. 28, 2013

(65) Prior Publication Data
US 2013/0261476 A1  Oct. 3, 2013

Related U.S. Application Data

(60) Provisional application No. 61/616,305, filed on Mar. 27, 2012.

(51) Int. Cl.
*A61N 1/08* (2006.01)
*A61B 5/04* (2006.01)
(Continued)

(52) U.S. Cl.
CPC ............ *A61B 5/04001* (2013.01); *A61B 5/686* (2013.01); *A61B 5/7221* (2013.01); *A61B 5/7246* (2013.01); *A61B 5/1107* (2013.01); *A61B 5/4052* (2013.01); *A61B 5/7217* (2013.01); *A61B 2562/0219* (2013.01)

(58) Field of Classification Search
USPC .................................. 600/510; 607/11, 17, 28
See application file for complete search history.

(56) References Cited

U.S. PATENT DOCUMENTS

| 7,142,919 B2 | 11/2006 | Hine et al. |
| 7,299,093 B2 | 11/2007 | Zhu et al. |
| 7,354,404 B2 | 4/2008 | Kim et al. |

(Continued)

FOREIGN PATENT DOCUMENTS

WO  WO-2013148053 A1  10/2013

OTHER PUBLICATIONS

U.S. Appl. No. 13/781,042, Non Final Office Action mailed May 15, 2014, 14 pgs.

(Continued)

*Primary Examiner* — Christopher D Koharski
*Assistant Examiner* — Michael Carey
(74) *Attorney, Agent, or Firm* — Schwegman Lundberg & Woessner, P.A.

(57) ABSTRACT

In an example, a system includes a cardiac pulse generator configured to generate cardiac paces to pace the heart, a sensor configured to sense a physiological signal for use in detecting pace-induced phrenic nerve stimulation where the pace-induced phrenic nerve stimulation is phrenic nerve stimulation induced by electrical cardiac pace signals, and a phrenic nerve stimulation detector configured to analyze the sensed physiological signal to detect PS beats where the PS beats are cardiac paces that induce phrenic nerve stimulation. The detector may be configured to correlate signal data for sensed beat signals to a PS template to detect PS beats, or may be configured to analyze morphological features of sensed beat signals to detect PS beats, or may be configured to detect PS beats using a combination that both correlates signal data for sensed beat signals to a PS template and analyzes morphological features of sensed beat signals.

20 Claims, 21 Drawing Sheets

(51) Int. Cl.
*A61B 5/00* (2006.01)
*A61B 5/11* (2006.01)

(56) References Cited

U.S. PATENT DOCUMENTS

| | | | |
|---|---|---|---|
| 7,426,412 B1 | 9/2008 | Schecter | |
| 7,477,932 B2* | 1/2009 | Lee et al. | 600/509 |
| 7,499,751 B2 | 3/2009 | Meyer et al. | |
| 7,636,599 B1 | 12/2009 | Koh et al. | |
| 7,972,276 B1 | 7/2011 | Min | |
| 8,326,418 B2 | 12/2012 | Sommer et al. | |
| 8,326,420 B2 | 12/2012 | Skelton et al. | |
| 8,626,292 B2 | 1/2014 | Mccabe et al. | |
| 8,634,915 B2 | 1/2014 | Mccabe et al. | |
| 2005/0145246 A1 | 7/2005 | Hartley et al. | |
| 2009/0043351 A1 | 2/2009 | Sathaye et al. | |
| 2009/0210024 A1 | 8/2009 | M. | |
| 2010/0262204 A1* | 10/2010 | McCabe et al. | 607/17 |
| 2010/0305637 A1 | 12/2010 | McCabe et al. | |
| 2010/0305638 A1 | 12/2010 | McCabe et al. | |
| 2010/0305647 A1 | 12/2010 | Mccabe et al. | |
| 2012/0035685 A1 | 2/2012 | Saha et al. | |
| 2012/0078320 A1 | 3/2012 | Schotzko et al. | |
| 2012/0296388 A1 | 11/2012 | Zhang et al. | |
| 2013/0060298 A1* | 3/2013 | Splett et al. | 607/28 |
| 2013/0261471 A1 | 10/2013 | Saha et al. | |
| 2013/0261688 A1 | 10/2013 | Dong et al. | |
| 2014/0005742 A1 | 1/2014 | Mahajan et al. | |
| 2014/0018872 A1 | 1/2014 | Siejko et al. | |
| 2014/0018875 A1 | 1/2014 | Brisben et al. | |
| 2014/0088661 A1 | 3/2014 | Hincapie Ordonez et al. | |
| 2014/0100626 A1 | 4/2014 | Mccabe et al. | |
| 2014/0128933 A1 | 5/2014 | Brooke | |
| 2014/0277244 A1 | 9/2014 | Rockweiler et al. | |
| 2014/0277280 A1 | 9/2014 | Saha et al. | |

OTHER PUBLICATIONS

U.S. Appl. No. 13/781,042, Response filed Aug. 12, 2014 to Non Final Office Action mailed 05-15-24, 14 pgs.
International Application Serial No. PCT/US2013/028315, International Search Report mailed Jul. 11, 2013, 3 pgs.
International Application Serial No. PCT/US2013/028315, Written Opinion mailed Jul. 11, 2013, 6 pgs.
"U.S. Appl. No. 13/781,042, Notice of Allowance mailed Oct. 15, 2014", 7 pgs.
"U.S. Appl. No. 14/191,193, Non Final Office Action mailed Oct. 28, 2014", 15 pgs.
"International Application Serial No. PCT/US2013/028315, International Preliminary Report on Patentability mailed Oct. 9, 2014", 8 pgs.

* cited by examiner

PHRENIC NERVE STIMULATION DETECTION

CLAIM OF PRIORITY

This application claims the benefit of priority under 35 U.S.C. §119(e) of Rockweiler et al., U.S. Provisional Patent Application Ser. No. 61/616,305, entitled "PHRENIC NERVE STIMULATION DETECTION", filed Mar. 27, 2012, which is herein incorporated by reference in its entirety.

TECHNICAL FIELD

This application is related generally to medical devices and, more particularly, to cardiac pacing systems, devices and methods that address unintended phrenic nerve stimulation.

BACKGROUND

Implanted pacing systems may be used to deliver cardiac resynchronization therapy (CRT) or to otherwise pace the heart. When the heart is paced in the left ventricle (LV), for example, there may be unwanted stimulation of the phrenic nerve that causes contraction of the diaphragm. Unintended phrenic nerve activation (an unintended action potential propagated in the phrenic nerve) is a well-known consequence of left ventricular pacing. The left phrenic nerve, for example, descends on the pericardium to penetrate the left part of the diaphragm. In most people, the left phrenic nerve runs close to the lateral vein. The unintended phrenic nerve activation may cause the diaphragm to undesirably contract. Unintended phrenic nerve activation may feel like hiccups to the patient. Such unintended phrenic nerve activation can occur when the electric field of the LV pacing lead is proximate to the left phrenic nerve and is at a stimulation output that is strong enough to capture the nerve.

Unintended phrenic nerve activation may vary from patient to patient. One reason for this variance is that the anatomic location of the phrenic nerve can vary within patients. Additionally, the veins are not always in the same location with respect to the ventricle and the nearby passing nerve. Also, the selected vein in which to place a cardiac lead for a prescribed cardiac therapy may vary.

Cardiac therapies may be delivered using different pacing configurations and different stimulation parameters. Examples of pacing configurations include LV bipolar, LV to can, and LV to RV (right ventricle) also referred to as "extended bipolar." Examples of stimulation parameters include the amplitude (e.g. voltage) and pulse width. The pacing configuration or the stimulation parameters of a therapy may be modified in an effort to avoid phrenic nerve stimulation.

For example, an implantation procedure may be modified to avoid phrenic nerve capture. For example, the LV pacing electrodes may be repositioned to capture the LV for a pacing therapy such as CRT while avoiding phrenic nerve capture, or the clinician may decide not to implant an LV pacing electrode but rather rely on other pacing algorithms that do not pace the LV.

Although phrenic nerve stimulation is commonly assessed at implant, unintended phrenic nerve activation caused by phrenic nerve capture during pacing may first appear or worsen post-implant for a variety of reasons such as reverse remodeling of the heart, lead micro-dislodgement, changes in posture, and the like. Therefore, special office visits after implant may be necessary or desirable to reprogram the device to avoid phrenic nerve stimulation.

SUMMARY

In an example of a method for detecting PS beats, the method may include pacing a heart with cardiac paces, sensing a physiological signal for use in detecting PS beats where sensing the physiological signal includes sensing beat signals from a window of time defined based on cardiac pace times, building a library of beat-type templates including storing beat signal data for the sensed beat signals in beat-type templates, and using the PS template to detect PS beats. Storing beat signal data may include determining if beat signal data for a currently-analyzed beat signal matches an existing beat-type template in the library, and creating a new beat-type template if there is no match or increasing a tally for the beat-type template if there is a match, and declaring that one of the beat-type templates to be a PS template when the tally for one of the beat-type templates reaches a defined threshold.

In an example of a method for detecting PS beats, the method may include pacing a heart with cardiac paces, sensing a physiological signal for use in detecting PS beats where sensing the physiological signal includes sensing beat signals from a window of time defined based on cardiac pace times, identifying morphological features for a sensed beat signal, and using the identified morphological features to determine if the sensed beat signal is a PS beat. Using the identified morphological features to determine if the sensed beat signal is a PS beat may include using weight-based scoring of the identified morphological features to analyze the identified morphological features. Using the identified morphological features to determine if the sensed beat signal is a PS beat may include using a decision tree to analyze the identified morphological features.

In an example of a method for detecting PS beats, the method may include pacing a heart with cardiac paces, sensing a physiological signal for use in detecting PS beats where sensing the physiological signal includes sensing beat signals from a window of time defined based on cardiac pace times, building a library of beat-type templates including storing beat signal data for the sensed beat signals in beat-type templates. Storing beat signal data may include determining if beat signal data for a currently-analyzed beat signal matches an existing beat-type template in the library, scoring the beat signal data for the sensed beat signals and creating a score-generated PS template from the beat signal data if there is no match to an existing beat-type template and if the score favorably compares to a defined threshold for the score, creating a new beat-type template if there is no match and the score does not favorably compare to the defined threshold for the score, and increasing a tally for the beat-type template if there is a match and declaring the beat type template to be a clustering-generated PS template when the tally reaches a defined tally threshold. The method may further include detecting PS beats using the score-generated PS template or the clustering-generated PS template.

In an example of a method for detecting PS beats, the method may include pacing a heart with cardiac paces, sensing a physiological signal for use in detecting PS beats where sensing the physiological signal includes sensing beat signals from a window of time defined based on cardiac pace times, scoring morphological features of the sensed beat signals, using the score to identify those sensed beat signals that can be declared PS beats with a high degree of confidence and those sensed beat signals that can be declared NoPS beats with a high degree of confidence, and correlating sensed beats that cannot be declared, with a high degree of confidence, as either a PS beat or a NoPS beat to a PS template, and declaring the sensed beats that are correlated with the PS template to be PS beats.

In an example, a system includes a cardiac pulse generator configured to generate cardiac paces to pace the heart, a sensor configured to sense a physiological signal for use in detecting pace-induced phrenic nerve stimulation where the pace-induced phrenic nerve stimulation is phrenic nerve stimulation induced by electrical cardiac pace signals, and a phrenic nerve stimulation detector configured to analyze the sensed physiological signal to detect PS beats where the PS beats are cardiac paces that induce phrenic nerve stimulation. The phrenic nerve stimulation detector may be configured to correlate signal data for sensed beat signals to a PS template to detect PS beats, or may be configured to analyze morphological features of sensed beat signals to detect PS beats, or may be configured to detect PS beats using a combination that both correlates signal data for sensed beat signals to a PS template and analyzes morphological features of sensed beat signals.

This Summary is an overview of some of the teachings of the present application and is not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
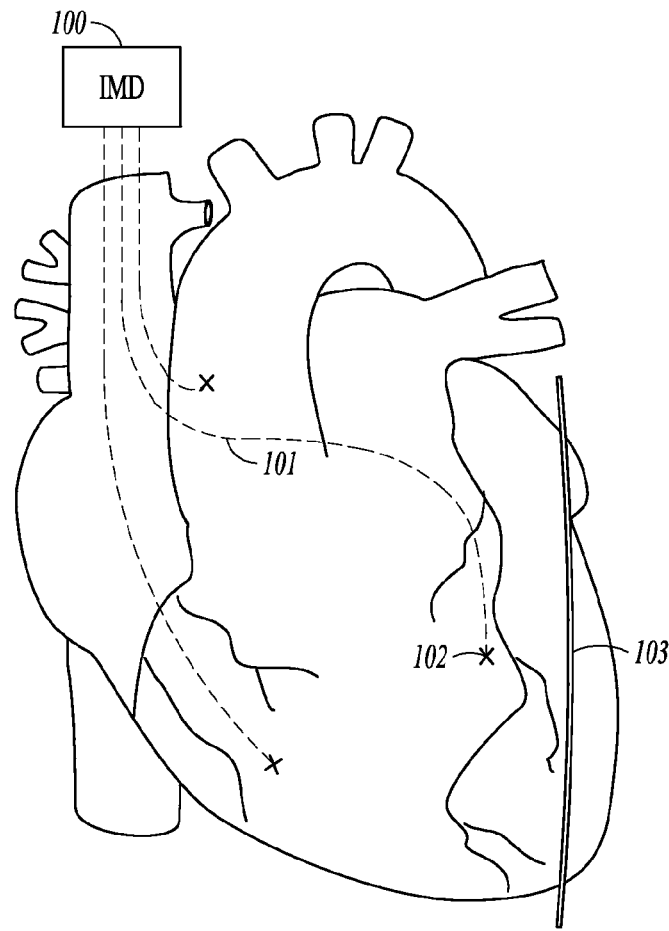
FIG. 1 illustrates, by way of example, an embodiment of an implantable medical device (IMD) configured to deliver myocardial stimulation.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Some embodiments, for example, implement an automatic detection algorithm for detecting unintended phrenic nerve activation (also referred to herein as pace-induced phrenic nerve stimulation or as phrenic nerve stimulation "PS"). According to various embodiments, the PS detection algorithm can be used in a clinical setting such as during implant procedures or in patient follow-up visits, or an ambulatory setting such as in a patient's home, or in both the clinical and ambulatory setting. The PS detection algorithm may lessen or alleviate the burden of the patients and clinical staff to adequately address the problems of unintended PS that may occur during myocardial stimulation. For example, the ability to accurately and/or automatically detect PS may reduce prolonged discomfort for patients experiencing PS, and may reduce the burden on hospitals and staff for testing and reprogramming devices.

The PS algorithm is capable of addressing problems with automatically detecting PS. Even when a patient is sitting quietly, it can be difficult to sense signals close to the PS threshold. For example, it can be difficult to process low-peak-to-peak amplitudes of sensed PS responses from the deflection variations observed in the accelerometer or other PS sensor, especially those close to the PS threshold. It can also be difficult to detect PS because different patients have PS response of various amplitudes.

Myocardial Stimulation

A myocardial stimulation therapy may deliver a cardiac therapy using electrical stimulation of the myocardium. Some examples of myocardial stimulation therapies, and devices for performing the therapies, are provided below. A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and then to the ventricular myocardium to provide a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure. Heart failure refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. A CRT example applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-myocardial infarction (MI) and heart failure patients, which appears to occur as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions may be the trigger for ventricular remodeling. Pacing one or more sites may cause a more coordinated contraction, by providing pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected. ATP may be referred to as overdrive pacing. Other overdrive pacing therapies exist, such as intermittent pacing therapy (IPT), which may also be referred to as a conditioning therapy.

Phrenic Nerves

Both a right phrenic nerve and a left phrenic nerve pass near the heart and innervate the diaphragm below the heart. Pace-induced phrenic nerve activation, also referred to herein as PS, may be observed with various forms of pacing. PS may be observed particularly with LV pacing because of the close proximity of the LV pacing site to the left phrenic nerve. PS is a common side effect of CRT. Cardiac stimulation at other locations of the heart may result in PS in either the left or right phrenic nerve. The present subject matter is not limited to PS of the left phrenic nerve during LV pacing, but may be implemented to appropriately address PS in either the left or right phrenic nerve caused by myocardial stimulation.

PS may be observed only when a patient is in a particular position (e.g. lying down) or activity level. The unintended phrenic nerve activation may not have been observed at the time that the stimulation device was implanted because of the patient position at the time of implantation, because of the effects of anesthesia, or because of other factors that are not present in a clinical setting. Some embodiments use a posture sensor to provide context. Some embodiments use an activity sensor to provide context. Some embodiments use a timer to determine a time of day to provide context. Some embodiments allow the device to store posture, activity, time of day and the like with the detected PS data to determine the context when the PS is observed.

FIG. 1 illustrates, by way of example, an embodiment of an implantable medical device (IMD) configured to deliver myocardial stimulation. The illustrated IMD 100 is used to perform a cardiac tissue stimulation therapy, such as CRT or other pacing therapies, using leads represented by the dotted lines and electrodes represented by "X" fed into the right atrium, right ventricle, and coronary sinus of the heart. The lead 101 passing through the coronary sinus of the heart includes a left ventricular electrode 102, or electrodes, for use to stimulate the left ventricle at a stimulation site. FIG. 1 also indicates that the left ventricular electrode 102 of the lead 101 is relatively close to the left phrenic nerve 103. PS may occur for certain configurations of pacing vectors or electrode placement. Various embodiments of the present subject matter may be used in processes for using PS sensor(s) to detect PS. A PS sensor is a sensor that may be used to detect unintended phrenic nerve activity. By way of example and not limitation, a PS sensor may include a sensor to detect motion caused by the diaphragm induced by PS. For example, some embodiments use an accelerometer to detect PS. Other examples of sensors that may be used to detect PS include, but are not limited to, an acoustic sensor, a respiration sensor, an impedance sensor, a neural sensor on the phrenic nerve, or an electromyogram (EMG) sensor for sensing signals indicative of diaphragm contraction.

Figure 2:
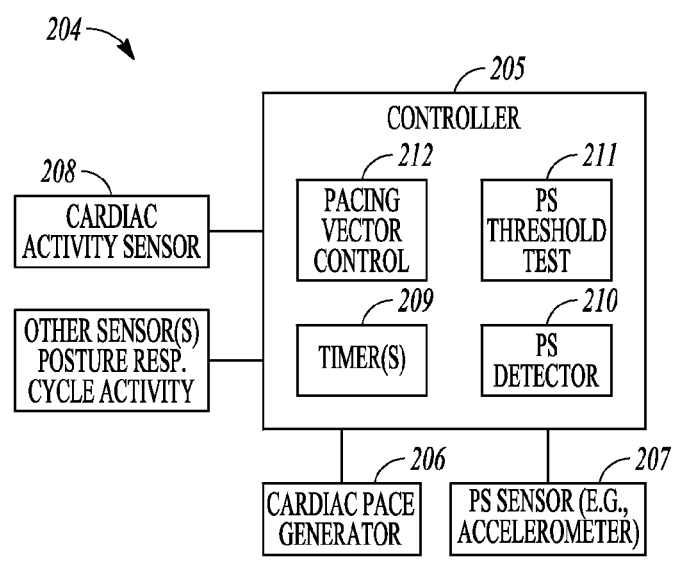
FIG. 2 illustrates, by way of example, an embodiment of an IMD.

FIG. 2 illustrates an embodiment of an implantable medical device (IMD). The illustrated IMD 204 may be used to deliver myocardial stimulation, and to detect PS unintentionally caused by the myocardial stimulation. The illustrated IMD 204 includes a controller 205, a cardiac pace generator 206, a PS sensor 207, and a cardiac activity sensor 208. In some embodiments, the IMD 204 may also include one or more other sensors such as, by way of example and not limitation, a sensor used for detecting posture, a sensor used for detecting respiration or a respiration cycle, or a sensor used for detecting activity. In some embodiments, the device implements a cardiac pacing algorithm, in which the controller 205 receives sensed cardiac activity from the cardiac activity sensor 208, uses timer(s) 209, such as a cardiac pacing timer, to determine a pace time for delivering a cardiac pace or other myocardial stimulation pulse, and controls the cardiac pace generator 206 to deliver the cardiac pace at the desired time. The controller 205 also includes a PS detector 210 that cooperates with the PS sensor 207 to discriminate if a signal from the PS sensor 207 is indicative of PS events.

In some embodiments, the IMD 204 may be configured with a PS threshold test module 211 used to perform PS threshold test(s). The PS threshold test may be configured to deliver myocardial stimulation using different stimulation parameters. The PS threshold tests may be configured to determine the myocardial stimulation parameters that cause or that may cause PS, or myocardial stimulation parameters that do not cause PS. The physical position of the stimulation electrode or electrodes used to deliver the myocardial stimulation may be adjusted in an attempt to avoid PS, such as may occur during an implantation procedure. A physician may physically move the electrode. Some embodiments may provide electronic repositioning by selecting a set of stimulation electrodes from a larger set of potential stimulation electrodes. In some embodiments, the pacing vector between or among stimulation electrodes may be modified in an attempt to avoid PS. The controller in some IMD embodiments may include a pacing vector control module 212 used to change the pacing vectors. The pacing vector control may be implemented under the control of a clinician through an external programmer, or may be implemented autonomously by the IMD such as may occur in an ambulatory setting.

Figure 3:
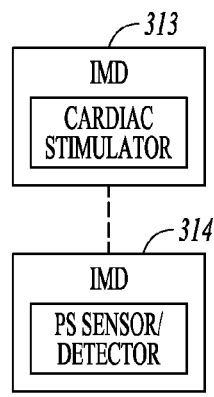
FIG. 3 illustrates, by way of example, an embodiment of a system that includes two or more IMDs.

The PS detection may occur in the same IMD that is providing the myocardial stimulation, or may occur in another IMD. Thus, for example, an accelerometer used to provide the PS detection may be positioned near the diaphragm or near the portion of the diaphragm innervated by the phrenic nerve or near the apex of the heart, which may improve the signal to noise characteristics of the sensed signal. FIG. 3 illustrates an embodiment of a system that includes two or more IMDs. A first one of the IMDs 313 in the illustrated system includes a cardiac stimulator configured to deliver myocardial stimulation pulses. By way of example and not limitation, the first IMD may be a pacemaker or other cardiac rhythm management device. A second one of the IMDs 314 in the illustrated system includes a PS detector/sensor used to detect PS that may be caused by the myocardial stimulation pulses delivered from the first one of the IMDs. In some embodiments, the IMDs 313, 314 may communicate with each other over a wired connection. In some embodiments, the IMDs 313, 314 may communicate with each other wirelessly using ultrasound or radiofrequency (RF) or other wireless technology.

The sensor(s) used for detecting PS may be implanted or may be external. The algorithms for processing the sensed signals to detect PS may be performed within the IMD(s) and/or may be performed in external devices. By way of example, some embodiments may use implantable sensor(s) and use external device(s) to process the sensed signals to detect PS. The monitoring of the patient for PS may be performed in a clinical setting or in an ambulatory setting. This monitoring, regardless of whether it is performed in the clinical setting or an ambulatory setting, may be performed using implanted PS detectors such as illustrated in FIGS. 2-3, for example, and/or may be performed using external PS detectors.

Figure 4:
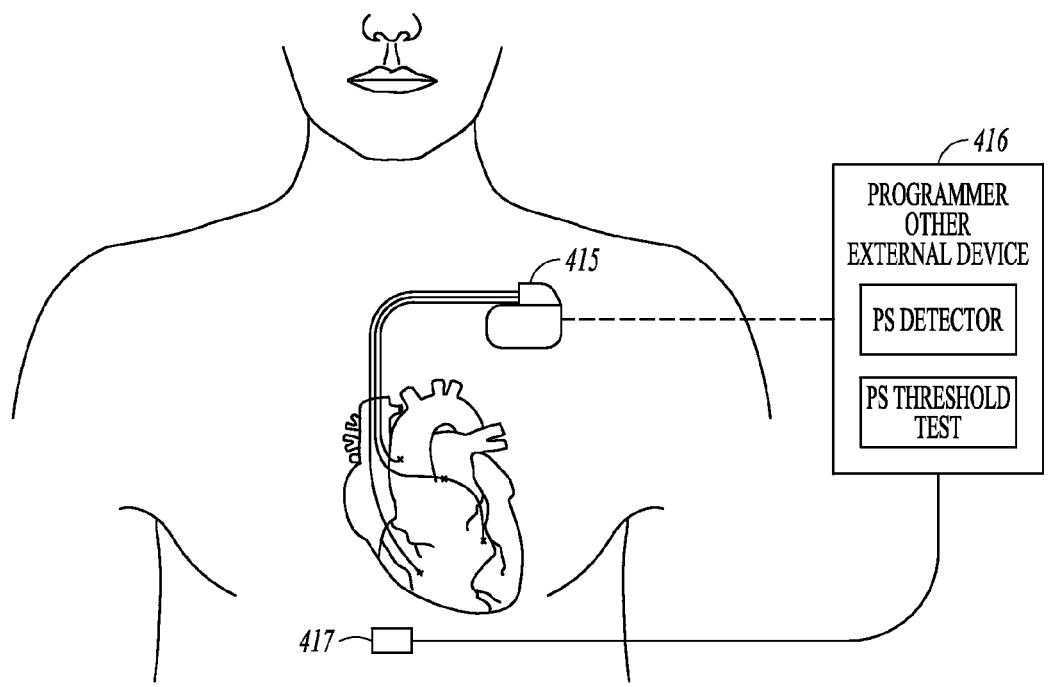
FIG. 4 illustrates, by way of example, an embodiment of a system that includes an IMD, an external device, and an external phrenic nerve stimulation (PS) sensor.

FIG. 4 illustrates an embodiment of a system that includes an IMD 415, such as a cardiac rhythm management device, an external device 416 such as a programmer, and an external PS sensor 417. The system may be implemented in a clinical setting, such as by a clinician who uses a programmer to program the IMD, or may be implemented by the patient in an ambulatory setting to occasionally check if the myocardial stimulation is causing PS. In various embodiments, the external device includes a PS detector that cooperates with the PS sensor to discriminate if a signal from the PS sensor indicates the presence of PS events. In various embodiments, the external device includes a PS threshold test module used to perform PS threshold test(s). The PS threshold test may be configured to control the IMD to deliver myocardial stimulation using different stimulation parameters. The PS threshold tests may be configured to determine the myocardial stimulation parameters that cause or that may cause PS, or myocardial stimulation parameters that do not cause PS. The physical position of the stimulation electrode or electrodes used to deliver the myocardial stimulation may be adjusted in an attempt to avoid PS, such as may occur during an implantation procedure. In some embodiments, the pacing vector between or among stimulation electrodes may be modified in an attempt to avoid PS. In some embodiments, the external PS sensor 417 may be integrated with the external device 416, such that the PS may be sensed by holding or otherwise positioning the external device next to the patient (e.g. externally positioned near the diaphragm or near the apex of the heart).

Figure 5:
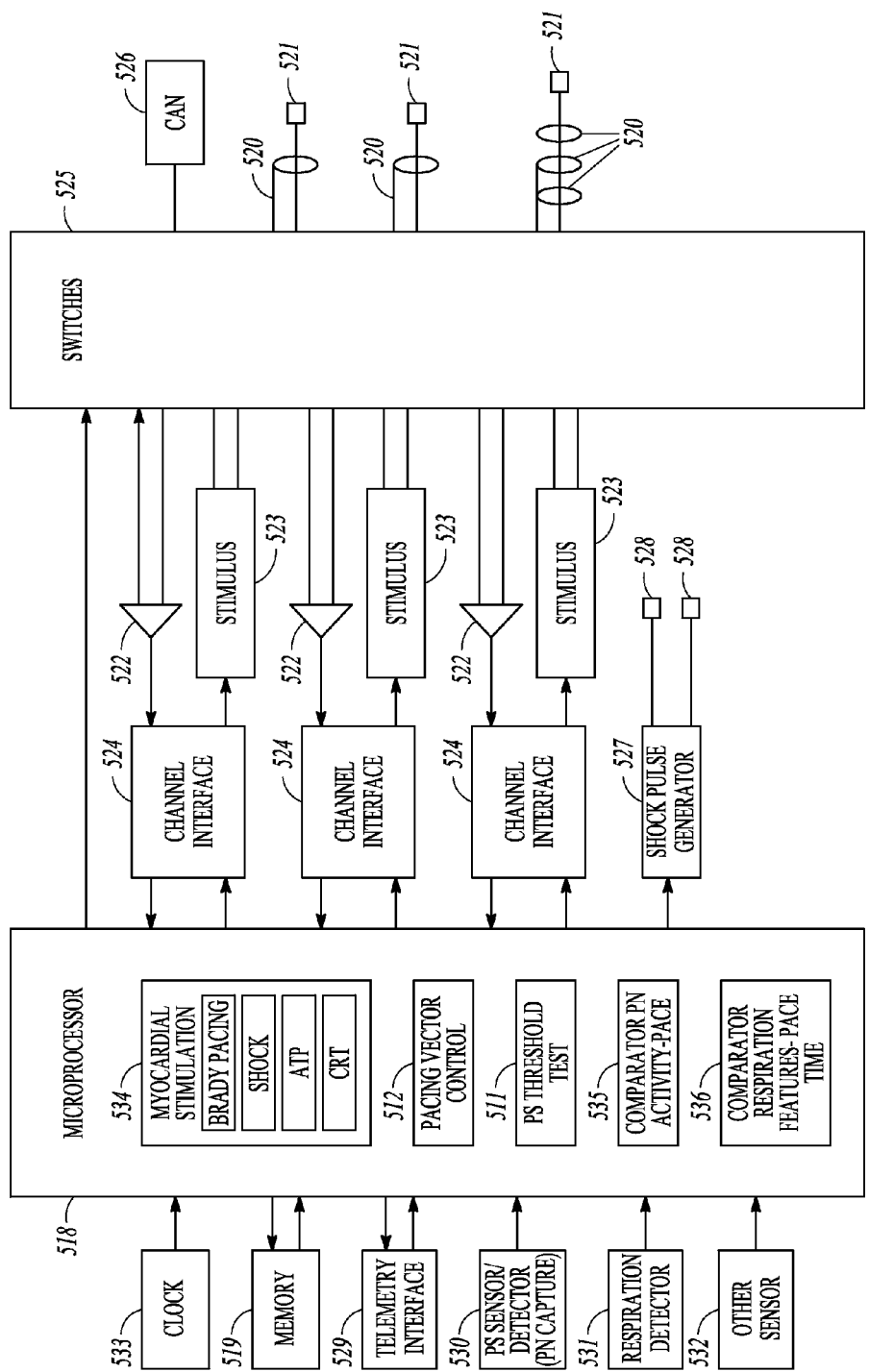
FIG. 5 illustrates, by way of example, a system diagram of an embodiment of a microprocessor-based implantable device.

FIG. 5 illustrates a system diagram of an embodiment of a microprocessor-based implantable device. The controller of the device is a microprocessor 518 which communicates with a memory 519 via a bidirectional data bus. The controller could be implemented by other types of logic circuitry (e.g., discrete components or programmable logic arrays) using a state machine type of design. As used herein, the term "circuitry" should be taken to refer to either discrete logic circuitry, firmware, or to the programming of a microprocessor. Shown in the figure are three examples of sensing and pacing channels comprising leads with ring electrodes 520 and tip electrodes 521, sensing amplifiers 522, pulse generators 523, and channel interfaces 524. One of the illustrated leads includes multiple ring electrodes 520, such as may be used in a multi-polar lead. An example of a multipolar lead is a left ventricle quadripolar lead. In some embodiments, the leads of the cardiac stimulation electrodes are replaced by wireless links. Each channel thus includes a pacing channel made up of the pulse generator connected to the electrode and a sensing channel made up of the sense amplifier connected to the electrode. The channel interfaces communicate bidirectionally with the microprocessor, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects intrinsic chamber activity, termed either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each lead are connected via conductors within the lead to a switching network 525 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in unipolar or an extended bipolar mode using only one of the electrodes of the lead with the device housing (can) 526 or an electrode on another lead serving as a ground electrode. In some embodiments, a shock pulse generator 527 may be interfaced to the controller, in addition or alternative to other stimulation channels, for delivering a defibrillation shock via a pair of shock electrodes 528 and 528 to the atria or ventricles upon detection of a shockable tachyarrhythmia. A can electrode may be used to deliver shocks. The figure illustrates a telemetry interface 529 connected to the microprocessor, which can be used to communicate with an external device. As illustrated in FIG. 5, the system may include a PS sensor/detector 530 used to detect unintended phrenic nerve activations caused by myocardial stimulation. Various embodiments may also include a respiration detector 531 and/or other sensor(s) 532 such as may be used to provide contextual information like activity and posture. According to various embodiments, the phrenic nerve activity detector may include, but is not limited to, an accelerometer, an acoustic sensor, a respiration sensor, impedance sensors, neural sensor on the phrenic nerve, or electrodes to sense electromyogram signals indicative of diaphragm contraction. Various embodiments use more than one detector to provide a composite signal that indicates phrenic nerve capture. The use of more than one detector may enhance the confidence in detecting PS events. The illustrated embodiment also includes a clock 533.

According to various embodiments, the illustrated microprocessor 518 may be configured to perform various cardiac tissue (e.g. myocardial) stimulation routines 534. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT). As illustrated, the controller 518 may also includes a comparator 535 to compare time when phrenic nerve activity is detected to a pace time to determine that phrenic nerve activity is attributed to the pace, and/or may includes a comparator 536 to compare respiration features to the pace time for use in detecting PS. The illustrated microprocessor 518 may include instructions for performing a PS threshold test 511 and a pacing vector control process 512, similar to the controller 205 illustrated in FIG. 2

Figure 6:
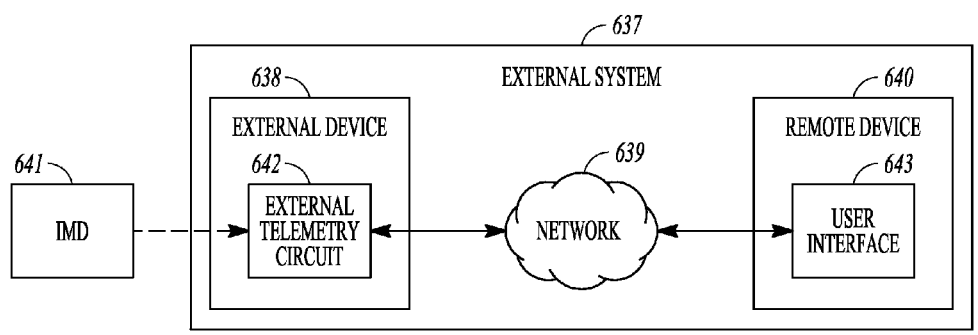
FIG. 6 is a block diagram illustrating, by way of example, an embodiment of an external system.

FIG. 6 is a block diagram illustrating an embodiment of an external system 637. For example, the system may be used to remotely program the implanted device in an ambulatory patient, or to remotely obtain detected PS events from an ambulatory patient, or to remotely retrieve sensed data from the implanted device in an ambulatory patient for analysis of the sensed data for the PS event in a remote location from the ambulatory patient. The external system includes a programmer, in some embodiments. In the illustrated embodiment, the external system includes a patient management system. As illustrated, the external system is a patient management system including an external device 638, a telecommunication network 639, and a remote device 640 removed from the external device 638. The external device 638 is placed within the vicinity of an implantable medical device (IMD) 641 and includes an external telemetry system 642 to communicate with the IMD 641. The remote device(s) is in one or more remote locations and communicates with the external device through the network, thus allowing a physician or other caregiver to monitor and treat a patient from a distant location and/or allowing access to various treatment resources from the one or more remote locations. The illustrated remote device includes a user interface 643. According to various embodiments, the external device includes a programmer or other device such as a computer, a personal data assistant or phone. The external device, in various embodiments, includes two devices adapted to communicate with each other over an appropriate communication channel, such as a computer by way of example and not limitation. The external device can be used by the patient or physician to provide feedback indicative of patient discomfort, for example.

According to various embodiments, various processes may be implemented using hardware, firmware, and/or software within the devices and systems discussed above for use in PS detection and determining PS threshold. These processes may be, but do not have to be, integrated within the same system. This document is organized to discuss some processes for baseline level determination, for PS detection, and for PS stimulation threshold determination.

Baseline Level Determination for PS Detection

Various embodiments may provide for a baseline level determination, which may be used to improve subsequent PS detection. An estimate for the baseline level of a sensor-based signal used in the PS detection may be used to perform Signal-to-Noise Ratio (SNR) calculations and to discriminate between NoPS (paced heart beats without PS) and PS beats (paced heart beats with PS). Some embodiments of the present subject matter may be configured to dynamically determine a baseline level of sensor-based signals used to detect PS, allowing the PS detector to automatically and accurately identify PS in the raw signal from the PS sensor. The dynamic determination of the baseline level improves the device's ability to automatically differentiate PS events from other events in the sensor signal by accommodating patient-specific differences in the sensed signal, and/or by accommodating context-specific differences in the sensed signal.

For example, although accelerometer-based PS sensor signals can vary in magnitude with pacing voltage, they demonstrate similar morphological features with different pulse widths, across different pacing configurations, across various postures over time and across patients. However, the PS detection should be adjusted appropriately in the presence of interference. For example, an accelerometer-based PS detector should accommodate baseline changes attributed to patient movement that can be detected by the accelerometer. PS detectors based on technology other than accelerometers also would benefit if the baseline was periodically adjusted to accommodate environmental or contextual changes that may be reflected as noise in the PS detector. For example, a respiration-based PS detector may have the baseline periodically adjusted to accommodate changes in the patient's activity or health. In another example, an accelerometer-based PS detector may have the baseline periodically adjusted to accommodate for patient activity, for patient environment (e.g. stationary or travel-induced vibrations), or for patient talking or other vocalization.

Figure 7:
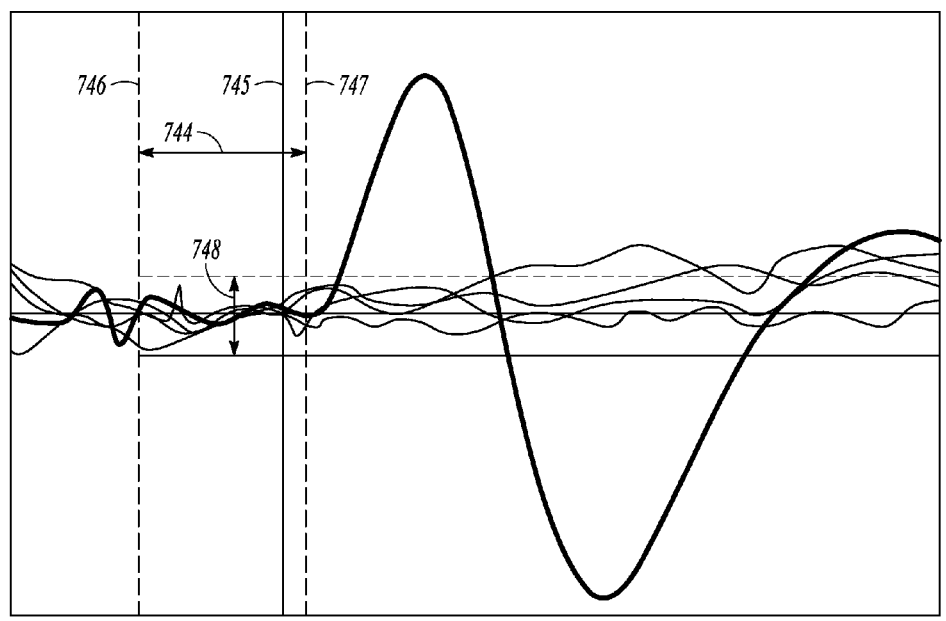
FIG. 7 illustrates, by way of example, sensor-based signals that may be used by a PS detector.

FIG. 7 illustrates sensor-based signals that may be used by a PS detector. The baseline level characteristics may be determined using signals collected from a baseline detection window 744 that is associated with a pace time (e.g. time of LV pace) 745 but that does not contain cardiac or PS components caused by the beat. For example, the baseline detection window may start at 746 prior to the pace timing and end at 747 before any cardiac component from the pace is expected and before a time that one would expect a PS component, if any, to occur after the pace. If the baseline detection window is associated with a sensed beat, the window may be triggered off of, by way of example, an R wave. The start and/or end times for the baseline detection window may be appropriately adjusted, depending on whether the detection window is triggered off of a sensed beat (e.g. sensed R wave) or triggered off of the pace. By way of example and not limitation, the baseline window may occur approximately 100 ms before a pace and extend 10 ms after the pace, where an accelerometer-based PS detector may be expected to detect a cardiac component more than 10 ms after the pace, and where the PS is also expected to occur, if at all, more than 10 ms after the pace. The baseline noise range 748 can be determined from the signal within this baseline detection window 744.

Figure 8:
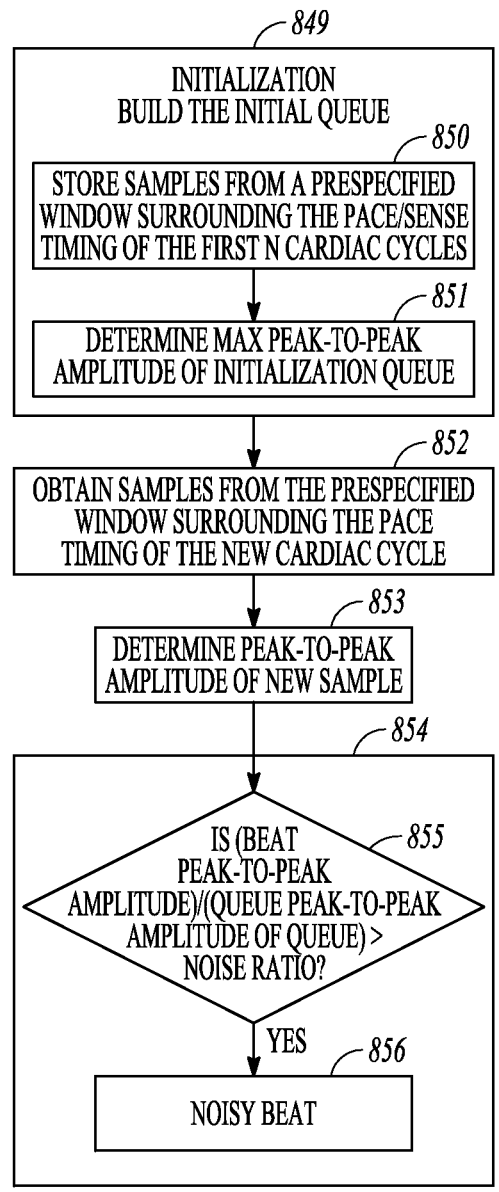
FIG. 8 illustrates, for example, an embodiment of a procedure to determine a baseline level of the sensor-based signal.

FIG. 8 illustrates, for example, an embodiment of a procedure to determine a baseline level of the sensor-based signal. During an initialization period 849, information from several beats is gathered in order to calculate an initial baseline level. About 20 beats may be averaged during the initialization period, by way of example and not limitation. In the illustrated procedure, sampled signal data from within the baseline detection window are stored in a queue for the first N cardiac cycles 850, and the maximum peak-to-peak amplitude of the signals is determined 851.

The baseline level characteristics can be updated with each new beat using a moving window. The characteristics of the baseline level may be compared to the beat characteristics in order to help differentiate between cardiac beats that cause PS ("PS beats") and cardiac beats that do not cause PS ("NoPS beats"). For example, a moving window of 20 beats may be used to determine an updated baseline level. In the illustrated procedure, sampled signal data from the baseline detection window is stored for a subsequent cardiac cycle 852, and the peak-to-peak amplitude is determined for the new sample 853.

In some embodiments, a beat is only included in the moving window if it satisfies certain criteria that indicates that it has a minimal level of noise that is not reflective of the baseline level. A beat amplitude may be required to fall within a peak-to-peak value. For example, the following equation may be used to define an acceptable peak-to-peak value for the beat: baseline level peak-to-peak=max((mean+2*SD)−(mean−2*SD)), where the mean and standard deviation (SD) are taken of all the valid samples in the queue for each time point. Various embodiments may provide a procedure to dynamically adjust the baseline level and to correct for baseline wandering while removing outlier beats which may not accurately reflect the change in the baseline level. In the illustrated procedure, a process to identify noisy beats as outlier beats to be removed may be implemented at 854. For example, a ratio of the peak-to-peak amplitude of the beat to the queue's peak-to-peak amplitude, which is reflective of the moving window, may be determined and compared to a noise ratio at 855. If the ratio is greater than a noise ratio, the beat is classified as a noisy beat 856, which should be ignored in determining the baseline level.

A baseline level determination procedure can be used as a standalone feature or in conjunction with a test for PS threshold or presence. For example, a baseline determination procedure can be implemented in test(s) that detect the presence of PS, and a baseline determination procedure can be implemented in test(s) that detect a PS threshold (e.g. a lowest pacing voltage for a pacing vector that is a PS beat). Since the baseline detection window is defined for a time period without cardiac components or PS components, it can be determined irrespective of the presence or absence of PS in the subsequent beat(s).

Various embodiments use context information to determine when to perform a baseline level determination process to dynamically adjust the baseline level. For example, contextual sensor, such as an activity or posture sensor, may be used to trigger the baseline level determination process. Some embodiments may trigger a baseline level determination process according to a schedule, which may be a programmed schedule to periodically or intermittently trigger the process. Some embodiments may trigger a baseline determination process based on a command received from a patient or clinician.

Some embodiments include attack and/or decay features to adjust the sensitivity to interference or noise. The attack and/or decay features may be programmable. Attack and Decay are features implemented with automatic gain control (AGC) systems. AGC systems are adaptive systems where the output level is used to appropriately adjust the gain for input signal levels. The attack and decay settings determine how fast the system responds to a changing signal input level. Attack indicates how quickly the gain is adjusted when the input level moves away from "normal," and decay indicates how quickly the gain returns back when the input signal returns toward "normal." Thus, the attack and decay settings determine how quickly the device responds to changes, including noise, in the input signal.

Figure 9:
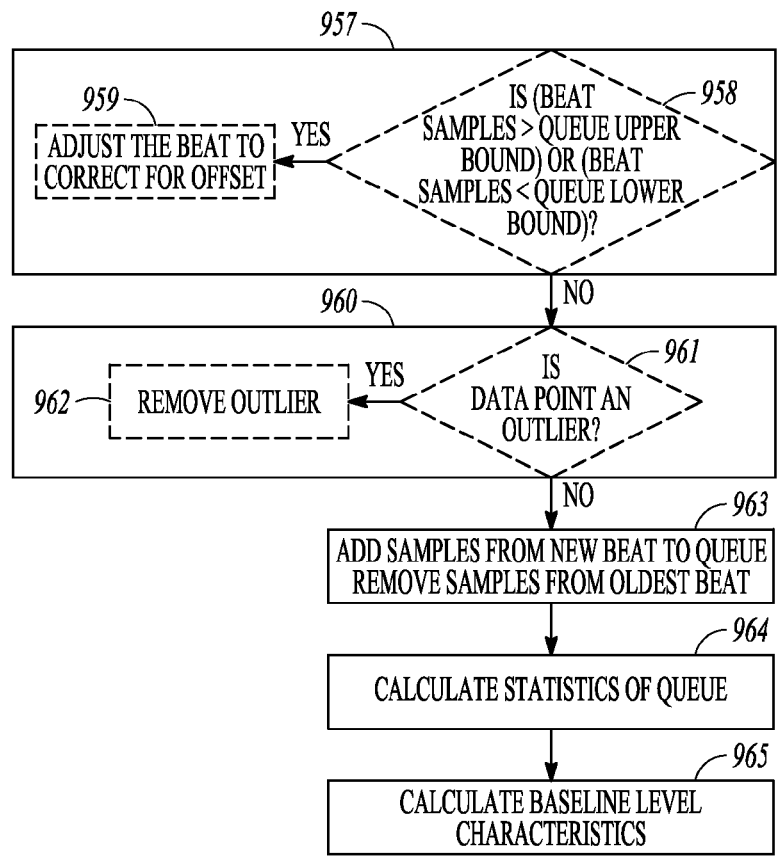
FIG. 9 illustrates, for example, an embodiment of a procedure for adding samples from new beats for a moving window used to determine a baseline level of the sensor-based signal.

FIG. 9 illustrates, for example, an embodiment of a procedure for adding samples from new beats for a moving window used to determine a baseline level of the sensor-based signal. Some embodiments may correct for a baseline offset if the beat samples are outside of upper or lower bounds 957. For example, a beat sample may be compared to the upper and lower bounds of the queue at 958. If the beat sample lies outside of the bounds, then the procedure may adjust the beat sample at 959 so that it lies within the upper and lower bounds of the queue before the beat sample is used by the procedure to dynamically adjust the baseline level.

Some embodiments may remove outlier data points from being used in the moving window to determine the baseline level 960. If a data point is determined to be a statistical outlier from the data points in the queue 961, then the outlier data point can be removed from being used in the procedure to dynamically adjust the baseline level 962. At 963, the new beat sample(s) is added to the queue, and the oldest beat sample(s) is removed from the queue. The statistics of the updated queue are calculated at 964. This may involve accumulating an ensemble of averages and standard deviations. The baseline level characteristics are calculated at 965. This may involve determining the peak-to-peak amplitude and the upper and lower bounds of the baseline level signal.

Figure 10:
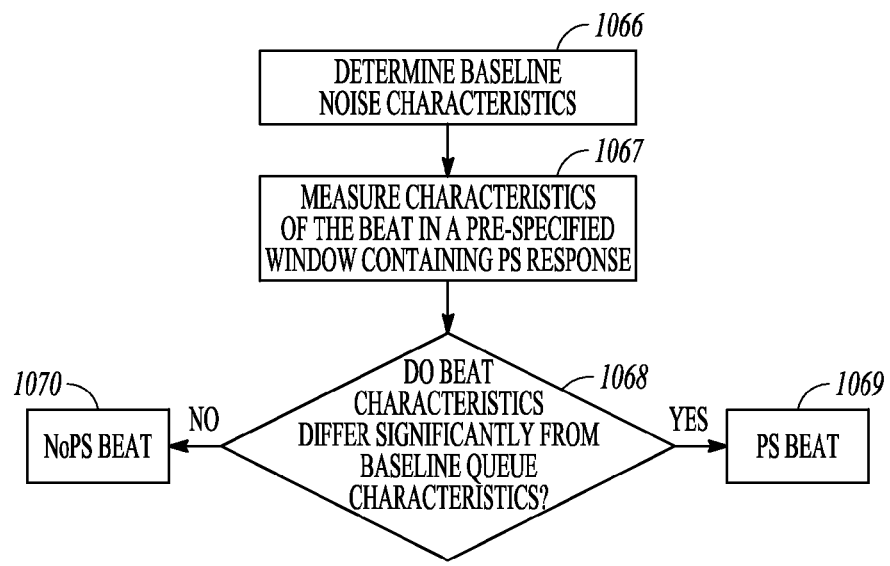
FIG. 10 illustrates, for example, an embodiment of a procedure for using the baseline level to discriminate between PS beats and NoPS beats.
Figure 11:
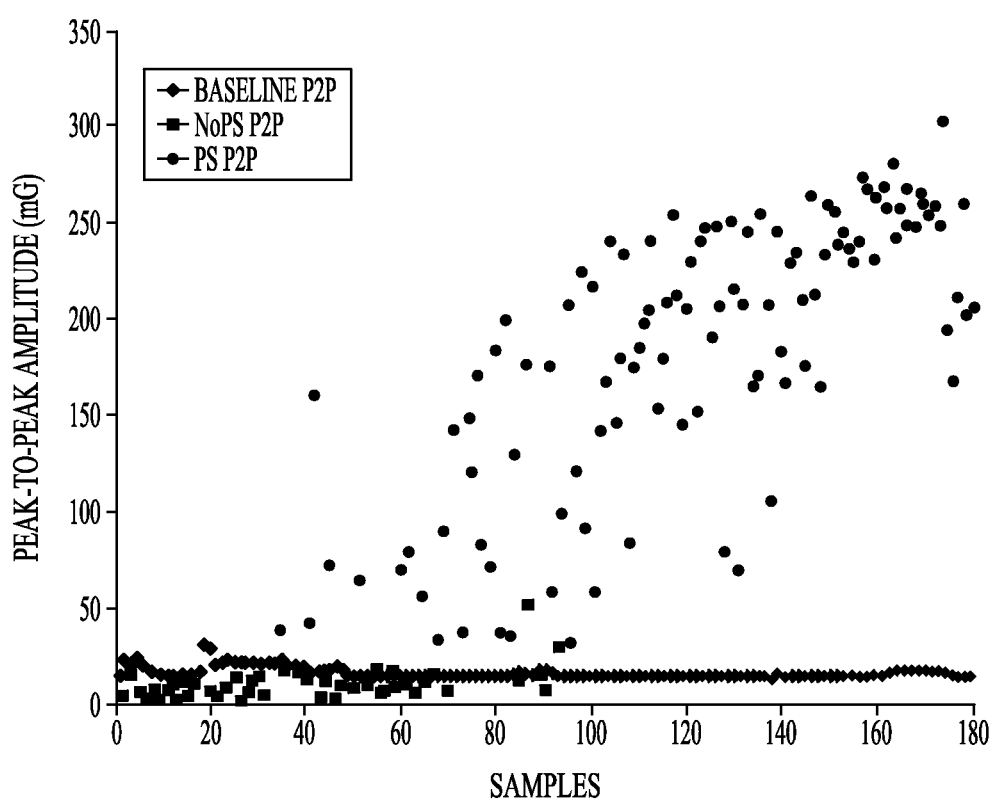
FIG. 11 is a plot of the peak-to-peak amplitude of sampled beats, which illustrates, by way of example, how the baseline peak-to-peak amplitude can be used to discriminate between NoPS beats whose peak-to-peak amplitudes are close to the baseline levels, and PS beats whose peak-to-peak amplitudes are significantly larger than the baseline levels.

FIG. 10 illustrates, for example, an embodiment of a procedure for using the baseline level to discriminate between PS beats and NoPS beats. At 1066, the baseline noise characteristics can be determined using procedures described above. A beat signal, which may or may not have caused a PS during a specified window of time, is analyzed to measure characteristics of the signal during the specified window 1067. This window of time for the beat signal is a different timing window than the window used to determine the baseline level, although they may overlap. This window of time for the beat signal typically spans a time after the pace which would include PS information if PS is present. At 1068, the characteristics of the beat signal are compared to the baseline level signal. The beat is classified as a PS beat 1069 if the characteristics of the beat signal differ significantly from the baseline signal, and is classified as a NoPS beat 1070 if the characteristics of the beat signal do not differ significantly from the baseline signal. For example, the peak-to-peak amplitude of the beat signal can be compared to the peak-to-peak amplitude of the baseline level to determine if there is a large enough difference to identify the beat signal as a PS beat. FIG. 11 is a plot of the peak-to-peak amplitude of sampled beats, which illustrates how the baseline peak-to-peak amplitude can be used to discriminate between NoPS beats whose peak-to-peak amplitudes are close to the baseline levels, and PS beats whose peak-to-peak amplitudes are significantly larger than the baseline levels.

This procedure may be implemented for ambulatory or in-clinic use. It may be implemented in a standalone PS detector, or in conjunction with a PS threshold test. The PS threshold test may be implemented alone as a standalone step-up and/or step-down test, or may be implemented in conjunction with a pacing threshold test (e.g. LV threshold) such that both the pacing threshold and the PS threshold are determined during the same test procedure.

In an example of a method for analyzing a sensed physiological signal to detect pace-induced phrenic nerve stimulation, the method may include sampling the sensed physiological signal during each of a plurality of cardiac cycles to provide sampled signals, calculating a baseline level for the physiological signal using the sampled signals, and detecting pace-induced phrenic nerve stimulation using the sensed physiological signal and the calculated baseline level. Sampling the sensed physiological signal may include sampling the signal during a time window defined using a pace time or using a sensed intrinsic beat (e.g. RV timing and LV offset) with each of the cardiac cycles to avoid cardiac components and phrenic nerve stimulation components in the sampled signal. Calculating the baseline level may include using the sampled signals stored in a queue to calculate the baseline level. The sensed physiological signal may be sampled during subsequent cardiac cycles to provide subsequent sampled signals, and the baseline level may be dynamically adjusted for the physiological signal using the subsequent sampled signals. Detecting pace-induced phrenic nerve stimulation using the sensed physiological signal and the calculated baseline level may include monitoring a beat signal within the sensed physiological signal where the beat signal is within a defined window of time that is defined using the pace time, identifying characteristics of the beat signal, comparing the characteristics of the beat signal to the baseline, and determining if the beat signal is a PS beat or a NoPS beat based on the comparison. PS beats are determined to include a pace-induced phrenic nerve stimulation response and NoPS beats are determined to not include the pace-induced phrenic nerve stimulation response. A baseline level determination process may be triggered according to a schedule or a sensed context or a patient-initiated or clinician-initiated command. The baseline level determination process may include sampling the signal during a time window defined using a pace time with each of the cardiac cycles to avoid cardiac components and phrenic nerve stimulation components in the sampled signal, and calculating a baseline level for the physiological signal using the sampled signals.

Some method examples may include pacing a heart with cardiac paces, sensing a physiological signal for use in detecting pace-induced phrenic nerve stimulation, performing a baseline level determination process to identify a baseline level for the sensed physiological signal, and detecting pace-induced phrenic nerve stimulation using the sensed physiological signal and the calculated baseline level. Detecting pace-induced phrenic nerve stimulation may include sampling the sensed physiological signal during each of a plurality of cardiac cycles to provide sampled signals and calculating the baseline level for the physiological signal using the sampled signals. Sampling the sensed physiological signal may include sampling the signal during a time window defined using a pace time with each of the cardiac cycles to avoid cardiac components and phrenic nerve stimulation components in the sampled signal.

In an example of a phrenic nerve stimulation detector configured to analyze a sensed physiological signal to detect a pace-induced phrenic nerve stimulation, the phrenic nerve stimulation detector may be configured to sample the sensed physiological signal during each of a plurality of cardiac cycles to provide sampled signals, calculate a baseline level for the physiological signal using the sampled signals, and detect pace-induced phrenic nerve stimulation using the sensed physiological signal and the calculated baseline level.

The signal may be sampled during a time window defined using a pace time with each of the cardiac cycles to avoid cardiac components and phrenic nerve stimulation components in the sampled signal. The phrenic nerve stimulation detector may include a memory for storing a queue of sampled signals, and may be configured to store the sampled signals in the queue and use the sampled signals stored in a queue to calculate the baseline level. The sensed physiological signal may be sampled during subsequent cardiac cycles to move subsequent sampled signals into the queue. The phrenic nerve stimulation detector may dynamically adjust the baseline level for the physiological signal using the subsequent sampled signals in the queue.

A system embodiment may include a cardiac pulse generator configured to generate cardiac paces to pace the heart, a sensor configured to sense a physiological signal for use in detecting pace-induced phrenic nerve stimulation, and a phrenic nerve stimulation detector configured to analyze the sensed physiological signal to detect the pace-induced phrenic nerve stimulation. The system may include at least one implantable medical device, including the cardiac pulse generator, the sensor and the phrenic nerve detector. The system may include at least one implantable medical device and at least one external device, where the implantable medical device includes the cardiac pulse generator, and the external device includes the phrenic nerve stimulation detector.

PS Detection

Various embodiments may use PS detection techniques, including clustering and correlation techniques to detect PS, feature-based techniques for detecting PS, and combinations thereof.

PS Detection Using Clustering and Correlation

Some embodiments of the present subject matter may be configured to detect the presence of PS based on the level of correlation between pace-gated sensor-based signals such as accelerometer signals. The term "pace-gated" indicates that the signal occurs during a window of time corresponding to a cardiac pace such as an LV pace, for example. If a cluster of beats (more than N beats) can be found with similar correlation, then those beats can be labeled as PS. According to some embodiments, the presence of phrenic nerve stimulation (PS) is determined based on the level of correlation between pace-gated sensor-based signals, such as accelerometer signals, for example. For example, a correlation coefficient can be calculated for the sensed signal and the template. By way of example and not limitation, a correlation algorithm may use a Pearson linear correlation and correlation coefficients (normalized covariance function). If a cluster of beats (e.g. more than N beats) can be found with similar correlation, those beats can be labeled as PS.

The systems and devices may be configured to trigger the procedures to classify beats using a variety of triggers. For example, the system or device may be commanded in-clinic or by an ambulatory patient to begin a procedure to classify the beats. A characteristic of the PS sensor signal may trigger the procedure. For example, if the amplitude of the signal is larger than a predetermined value, then the system or device may be triggered to classify the beats. Some embodiments continuously classify beats in an ambulatory setting. The beat classification may be triggered with a pace threshold test. When the procedure is triggered, a template library is generated based on the XL sensor signal response to a pace. As the accelerometer signal is read, it can be determined whether the beat matches a previous beat template in the library or not. This matching decision is based on the correlation between the current beat and the template. If the beat does not match any template already stored in the library, and there is still room to store more templates, the current beat's template is added to the library. If the beat does match a template that is already stored, the tally for that template is increased by one and the template is optionally updated with the latest beat information. Once the tally exceeds some threshold value, the template and all beats that match it (past and future) are labeled PS. In addition, the algorithm can also assess whether or not a cardiac beat caused PS ("PS beat") or did not cause PS ("No PS beat") at any time with any template.

The PS template may be a template generated by the library method described above, or, it may be provided by physician input, patient input, a population-based pre-programmed template, or other means. The sensor-based signal may be analyzed in a certain window around the pace, and then correlated with the PS template. If the correlation is high, then the current beat may be labeled a PS beat. If the correlation is not high, then the current beat may be labeled a NoPS beat.

PS detectors use sensor-based signals to determine when PS occurs. An example of a sensor-based signal is an accelerometer signal. However, the correlation process for detecting PS may be implemented with other PS detectors that are not accelerometer based. For example, PS sensor signals such as impedance, muscle activity, respiration, nerve activity, and the like may be analyzed, in a certain window around the pace, and correlated with the PS template to determine if the pace is a PS beat or a NoPS beat.

This procedure may be implemented for ambulatory or in-clinic use. It may be implemented in a standalone PS detector, or in conjunction with a PS threshold test. The PS threshold test may be implemented alone as a standalone step-up and/or step-down test, or may be implemented in conjunction with a pacing threshold test (e.g. LV threshold) such that both the pacing threshold and the PS threshold are determined during the same test procedure. The voltage or pulse width of the pace may be adjusted to provide a desired NoPS pace that captures the myocardial tissue.

The sensing window can be defined relative to a pace time. For example, if concerned about LV pacing causing PS, the sensing window can be defined relative to an LV pace time or relative to an RV pace time plus an LV offset. By way of examples, and not limitation, the window may be defined to be about 20 ms to 100 ms, or may be defined to be about 40 ms to 70 ms after the LV pace. Other ranges may be used. Such windows help avoid heart sounds or other noise in the sensed signals.

According to various embodiments, all data points, or certain data points, or select features of the PS sensor signal within the sensing window may be correlated to the template signal. A "match" can be declared, indicating a PS beat, if the signal or a portion of the signal within the sensing window exceeds a certain degree of correlation (e.g. >0.9) with the PS template in the library.

The templates in the library may be adjusted, according to some embodiments. For example, the templates can be adjusted by an average (weighted, moving, etc.) of all beats assigned to that beat type. An amplitude or other feature of the signal for a beat may be compared to criteria for that feature before adding a new template to the library. In addition, feature(s) of the processed signal, such as a first-order derivative, a multiple-order derivative, or an integral, may be compared to criteria for the feature(s).

The beat-template library may be built using a limited number of templates stored over time. When max storage has been reached, the template with the least matches (i.e. lowest tally) is dropped from the library. Each beat's correlation to the templates in the library is assessed. A defined correlation threshold can be used to identify when a beat matches a template. Every time the beat matches a template, a tally of the beat matches for that template is increased. Once a determined number of matches have been found, the template and all beats which match it are declared PS beats.

Figure 12:
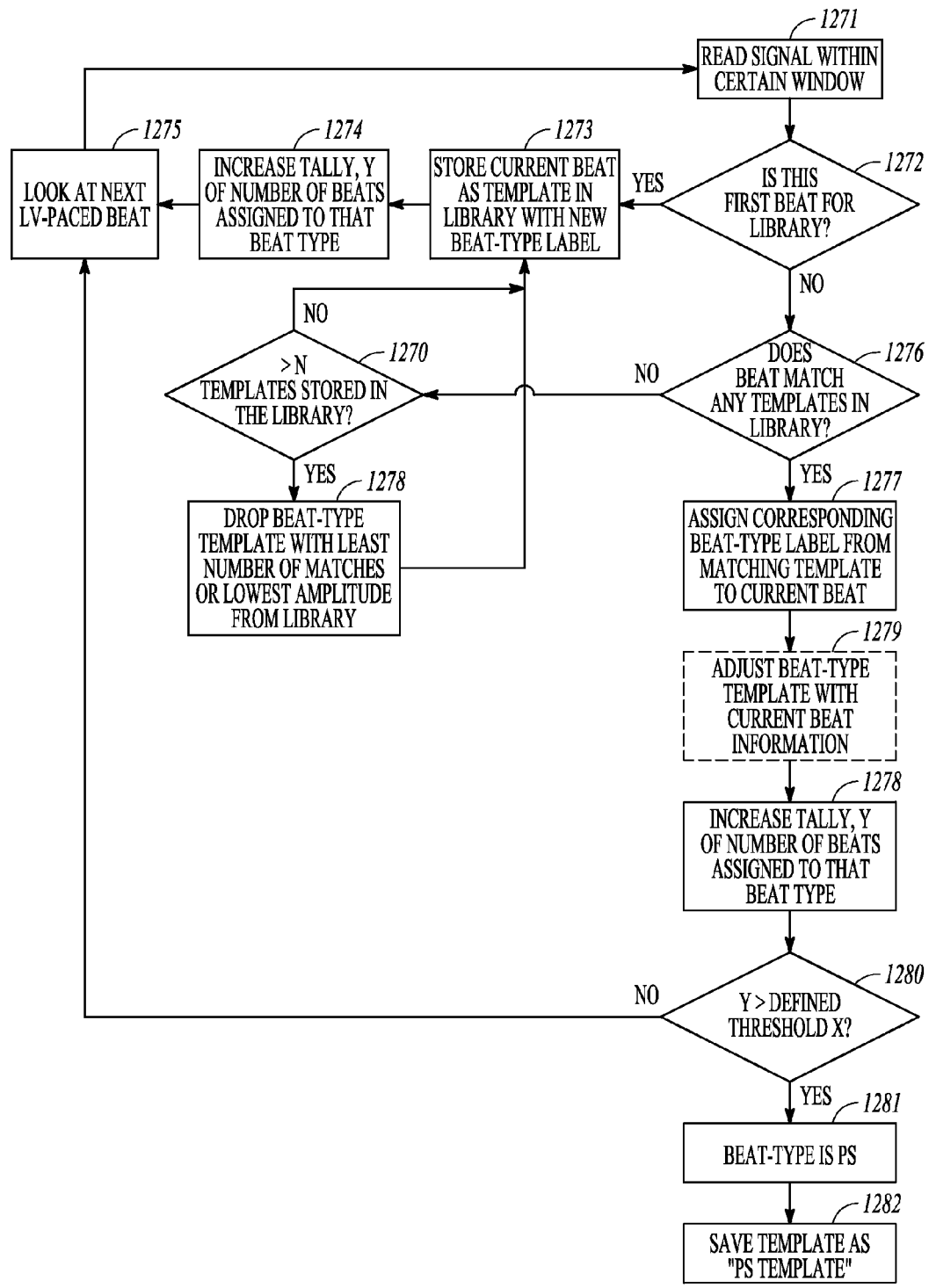
FIG. 12 illustrates, by way of example, an embodiment of a procedure for developing a library of PS templates that may be used to discriminate between PS beats and NoPS beats.

FIG. 12 illustrates, by way of example, an embodiment of a procedure for developing a library of PS templates that may be used to discriminate between PS beats and NoPS beats. At 1271, a sensor-based signal, such as an accelerometer signal, is sensed within a defined window of time with respect to a pace, referred to herein as a sensed "beat signal" to indicate that the sensed signal corresponds with a paced beat. If the sensed beat signal is the first in the library, as illustrated at 1272, then the current beat signal is stored as a template within the library, and is identified with a new beat-type label 1273. The procedure tracks the number of beat signals that have been classified as a given beat-type, and uses this number to compile the templates in the library. After the current beat signal is stored as a beat-type template at 1273, a tally of the number of beats assigned to the beat type is incremented at 1274, and the process proceeds to analyze the next paced beat (e.g. LV pace) at 1275. If the sensed beat signal is not the first in the library, as illustrated at 1272, then the procedure analyzes the beat signal to determine if the beat signal matches an existing beat-type template in the library 1276. If the beat signal does not match an existing beat-type template, then the current beat signal is stored as a template with a new beat-type label 1273 and the tally for that beat-type template is increased at 1274, assuming that a limit for the number of templates for the library has not been reached, as represented at 1270. If the limit for the number of templates has been reached, then a beat-type template is removed from the library at 1278 before the current beat signal is stored as a beat-type template. The criteria for removing a template may be based on the template with the lowed tally of beat signals that match the template, or based on the lowest amplitude, or based on a combination thereof. Other criteria may be used for dropping beat-type templates from the library. If a beat signal matches an existing template in the library 1276, then the beat signal is identified as a match to the beat-type template 1277 and the tally of the number of beat assigned to the beat type is incremented at 1278. Some embodiments may further adjust the beat-type template using the current beat signal, as represented at 1279, to further fine-tune the signal characteristics that can be used to categorize a beat signal as matching that specific beat-type template. After the tally for the beat-type template reaches a defined threshold 1280, then that beat-type template is identified as a PS template 1281 and saved in the library as a PS template 1282. The process may stop with one PS template, or may continue to develop more PS templates for storage in the library for use in discriminating between PS beats and NoPS beats.

Figure 13:
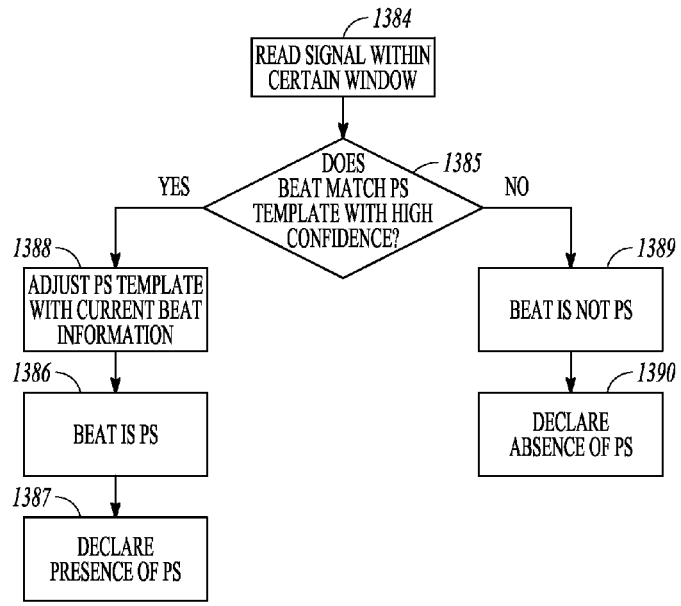
FIG. 13 illustrates, by way of example, an embodiment of a procedure for using PS templates to discriminate between PS beats and NoPS beats.

FIG. 13 illustrates, by way of example, an embodiment of a procedure for using PS templates to discriminate between PS beats and NoPS beats. The PS template may be determined using a procedure similar to the procedure illustrated in FIG. 12, or may be provided using other methodologies. For example, the template may be provided by a correlation library, a PS threshold test, a morphological determination, a physician input, or a patient input. The template may be patient specific or may be a population-based pre-programmed template. A sensor-based signal used for PS detection is sensed within a window defined with respect to a paced event 1384. This sensed signal may be referred to as a beat signal. If the beat signal is determined to match a PS template 1385, then the beat signal is identified as a PS 1386 and the system can declare the presence of PS 1387. Some embodiments may further adjust the PS template using the current beat signal, as represented at 1388, to further fine-tune the signal characteristics that can be used to categorize a beat signal as PS. If the beat signal is determined not to match a PS template 1385, then the beat signal is identified as a NoPS beat 1389 and the system can declare the absence of PS 1390. The determination of whether a beat signal matches a PS template may have a confidence factor, such that PS is only declared if there is a high confidence that the beat signal is PS. A confidence factor may also be used to create more than just a PS beat category or a NoPS category. For example, an "Unsure" category may be used.

Figure 14:
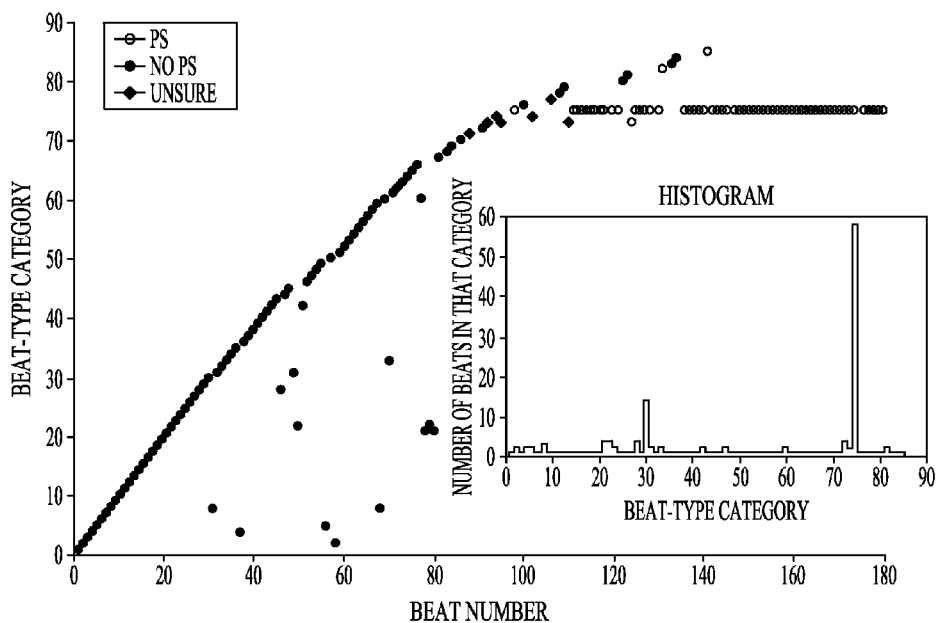
FIG. 14 illustrates a plot of beat signals against beat-type categories, and a corresponding histogram that plots out a number of beat-type categories and the number of beats that have been tallied in that category.

FIG. 14 illustrates a plot of beat signals against beat-type categories, and a corresponding histogram that plots out a number of beat-type categories and the number of beats that have been tallied in that category. The figure illustrates that the present subject matter can identify PS with a high degree of confidence.

Feature-Based PS Detection

Some embodiments of the present subject matter may be configured to detect the presence and threshold of phrenic nerve stimulation based on morphological features of collected sensor-based signals, allowing the PS detector to automatically and accurately identify PS in the raw signal from the PS sensor. This procedure may be used with a PS threshold test or with a test for detecting the presence of PS. This procedure may be implemented for ambulatory or in-clinic use. It may be implemented in a standalone PS detector, or in conjunction with a PS threshold test. The PS threshold test may be implemented alone as a standalone step-up and/or step-down test, or may be implemented in conjunction with a pacing threshold test (e.g. LV threshold) such that both the pacing threshold and the PS threshold are determined during the same test procedure. The voltage or pulse width of the pace may be adjusted to provide a desired NoPS pace that captures the myocardial tissue. The systems and devices may be configured to trigger the procedures to classify beats using a variety of triggers. For example, the system or device may be commanded in-clinic or by an ambulatory patient to begin a procedure to classify the beats. A characteristic of the PS sensor signal may trigger the procedure. For example, if the amplitude of the signal is larger than a predetermined value, then the system or device may be triggered to classify the beats. Some embodiments continuously classify beats in an ambulatory setting. The beat classification may be triggered with a pacing threshold test.

Certain morphological parameters, such as peak timing and amplitude and peak-to-peak amplitude are used to classify beats as PS beats or NoPS beats. Features may be derived from PS sensor signals (e.g. accelerometer signals) that are observed soon after the pace. The features can be compared to certain independent weight-based criteria in order to assign a score to each beat. Features may have a positive or negative weight, depending on propensity of the feature for being indicative of a PS or NoPS beat. The score for the beat is compared to a predetermined threshold to classify the beat as a PS or NoPS beat. Alternatively or in addition to scoring the features, the features can be compared using a decision tree to provide an overall score. By using both a scoring algorithm and decision tree, the procedure can quickly determine those beats that can be quickly identified as PS beats because of a high amplitude, for example. The procedure can improve the classification of and bolster confidence in the classification of lower amplitude PS beats. A confidence level on the final beat classification may be issued.

Examples of morphological features that can be used in the feature-based PS detection include, but are not limited to: peak timing and amplitude, peak-to-peak amplitude, slope to and away from peak, timing and amplitude of previous and following extrema, area under the curve, signal frequency components, and significant points.

A confidence level of the decision may be determined and provided with the PS beat or NoPS beat decision. For example, if the beat score is much greater than a scoring threshold, a high confidence indicator can be provided with the decision. However, if the beat score is close to the scoring threshold, a low confidence indicator can be provided with the decision. A confidence level may also be determined using both algorithms to separately classify PS, where the classification includes a high confidence indicator if both algorithms agree and/or the classification includes a low confidence indicator if the algorithms do not agree with each other.

Figure 15:
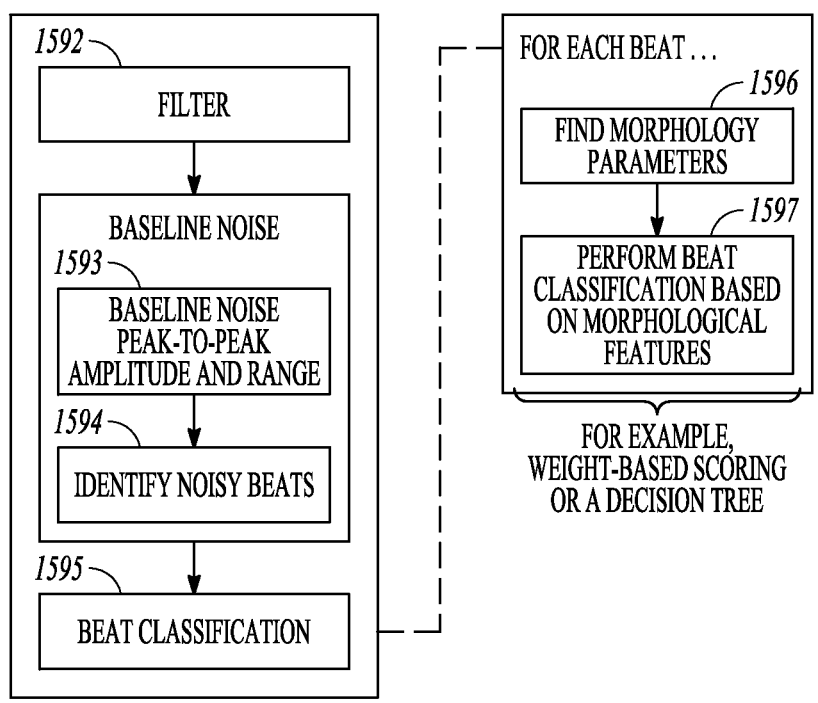
FIG. 15 illustrates, by way of example, an embodiment of a procedure for using morphological features of a sensor-based signal to discriminate between PS beats and NoPS beats.
Figure 16A:
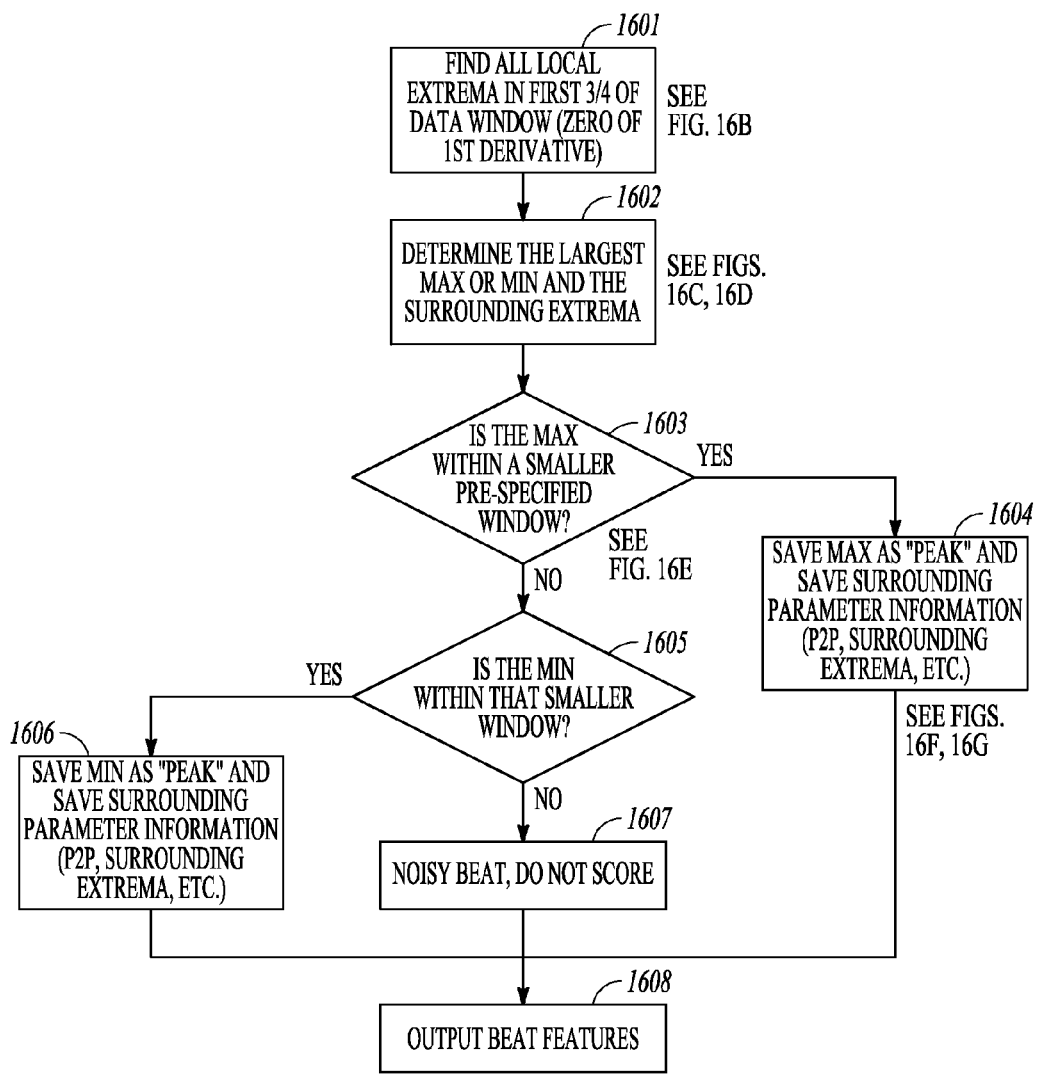
FIGS. 16A-16G illustrate, by way of example, an embodiment of a procedure for using signal peaks, as a morphological feature for a sensor-based signal, to discriminate between PS beats and NoPS beats.
Figure 16B:
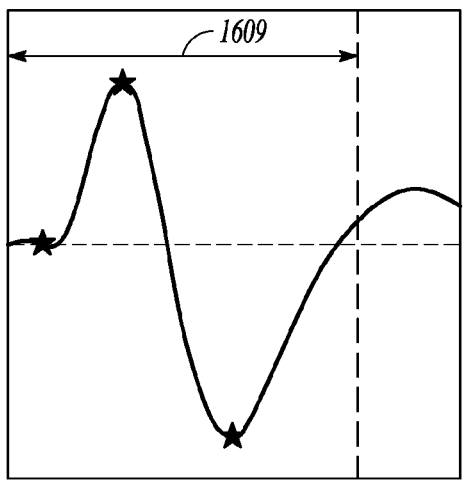
Figure 16C:
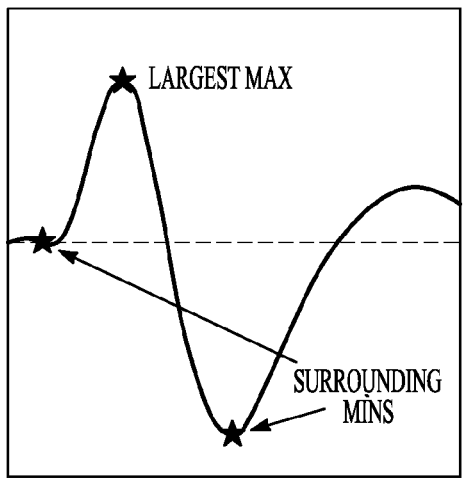
Figure 16D:
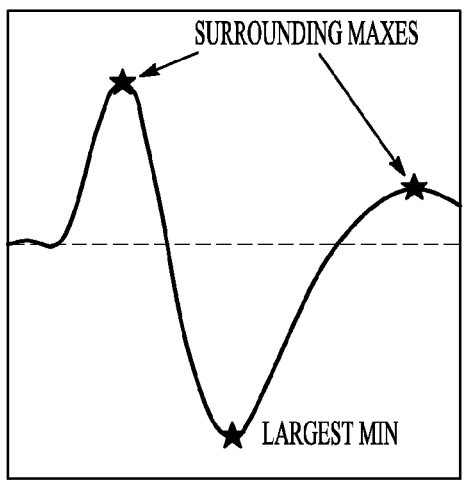
Figure 16E:
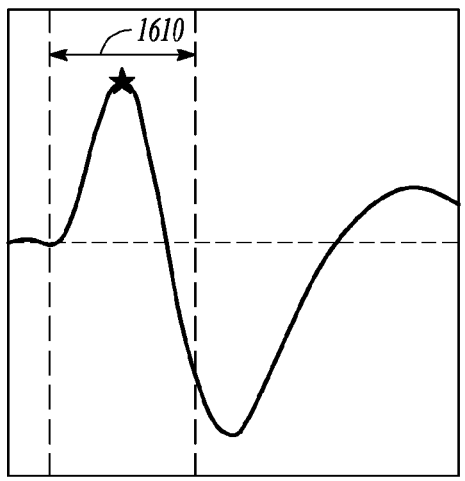
Figure 16F:
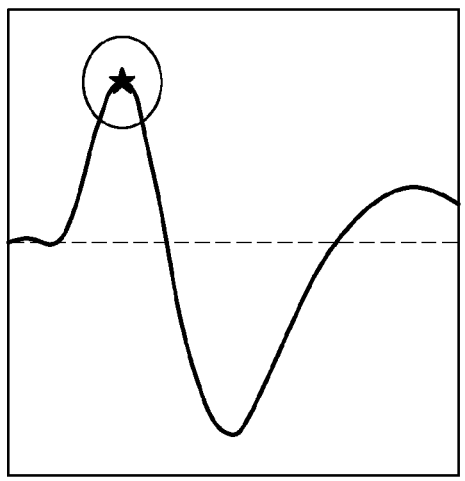
Figure 16G:
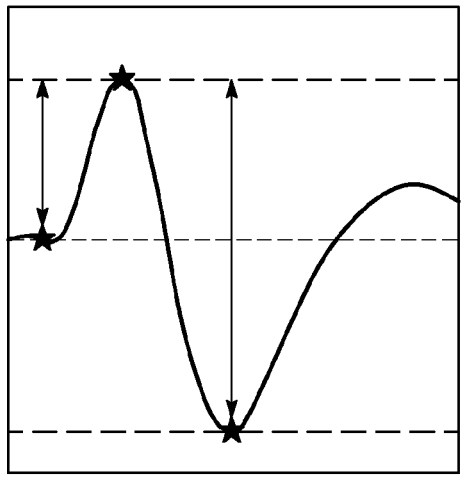

FIG. 15 illustrates, by way of example, an embodiment of a procedure for using morphological features of a sensor-based signal to discriminate between PS beats and NoPS beats. In the illustrated embodiment, for example, a sensed signal may be filtered 1592. Baseline signal levels 1593 may be used to identify and remove noisy beats 1594 from the discrimination procedure. The remaining beat signals can be classified as PS beats or NoPS beats at 1595. For example, as illustrated at 1596 the beat signal is analyzed to identify morphological parameters that can be used to characterize specific features of the beat signal, which can then be used to classify the beat signal, at 1597, using a weight-based scoring methodology, or a decision tree methodology, or a combination thereof.

FIGS. 16A-16G illustrate, by way of example, an embodiment of a procedure for using signal peaks, as a morphological feature for a sensor-based signal, to discriminate between PS beats and NoPS beats. The beat signal represents a sensed signal within a window defined in relation to a pace. At 1601, the local extrema can be determined for data in a first window of time 1609, using zero crossing of a first derivative of the signal. The local extrema can be compared to identify the maximum and minimum peaks 1602. At 1603 it may be determined if the maximum extremum occurs in a smaller window of time 1610. If the maximum extremum occurs within this smaller window of time, then the maximum extremum can be saved as a peak, as illustrated at 1604, along with surrounding parameter information such as surrounding extremas and peak-to-peak values. If the maximum extremum does not occur within this smaller window of time, then it may be determined if the minimum extremum occurs within that window, as illustrated at 1605. If the minimum extremum occurs within this smaller window of time, then the minimum extremum can be saved as a peak, as illustrated at 1606, along with surrounding parameter information such as surrounding extremas and peak-to-peak (P2P) values. If neither the maximum extremum nor the minimum extremum are within the smaller window of time, then the beat signal may be analyzed to determine if it is a noisy beat 1607, in which case the beat would not be scored. The features of the beat signal can then be output for scoring 1608.

Figure 17:
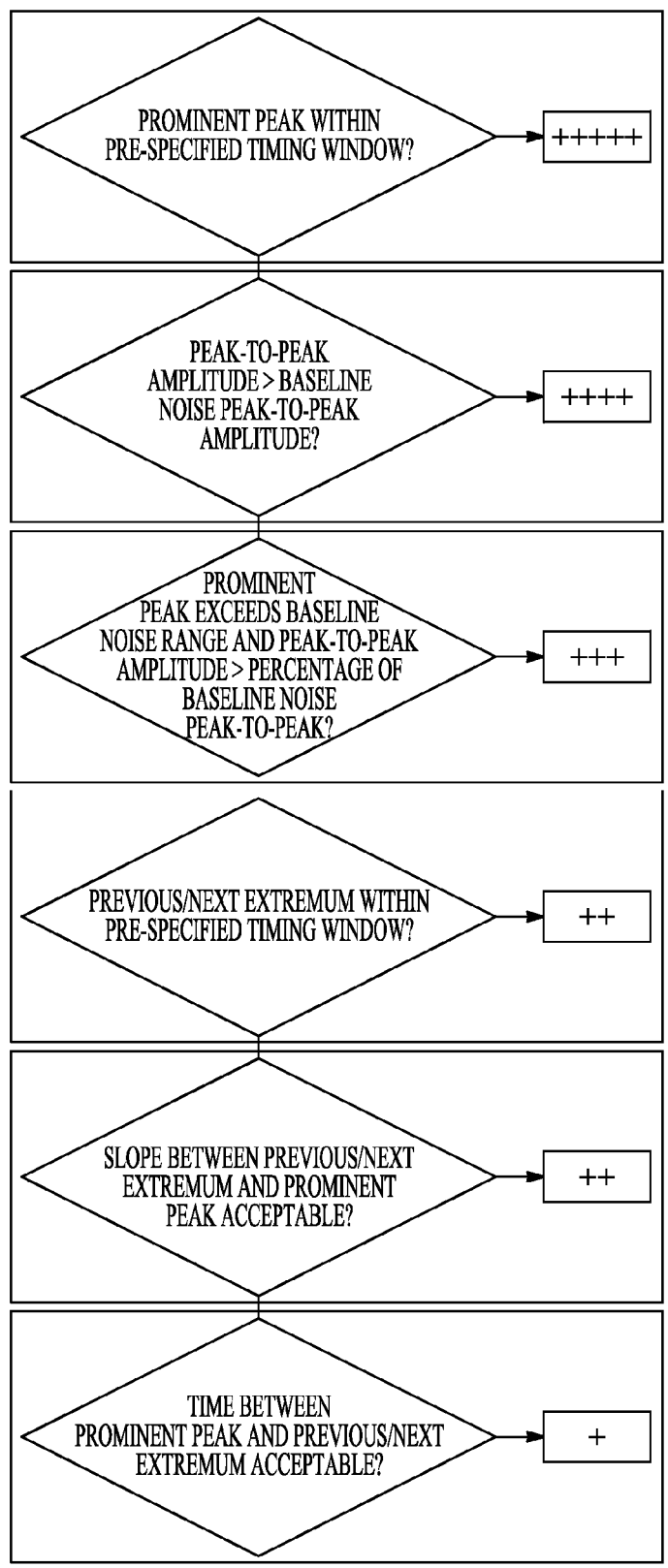
FIG. 17 illustrates, by way of example, an embodiment of a procedure for scoring sensed parameters for specific morphological features.

FIG. 17 illustrates, by way of example, an embodiment of a procedure for scoring sensed parameters for specific morphological features. The figure generally illustrates that certain features can be weighted more heavily than other features when analyzing the beat signal to determine whether the beat signal should be classified as a PS or a NoPS beat. The illustration uses multiple "+" symbols for some features that, in the illustrated example, may be considered higher priority features to be weighted more heavily. Examples of features that may be analyzed and scored include whether there is a prominent peak within a defined timing window, whether and how much greater then peak-to-peak amplitude is compared to the baseline level, whether a previous extremum is within a specified timing window, whether a slope between extrema is acceptable and whether a time between extrema is acceptable. Various criteria for various beat signal parameters may be used. Additionally, the criteria may be weighted in a number of ways to derive an overall score for the beat signal, which can then be used to discriminate between PS and NoPS beats. For example, a beat can be labeled a PS beat when the score exceeds a threshold. The criteria may be evaluated independently, and need not be evaluated in a particular order.

Figure 18:
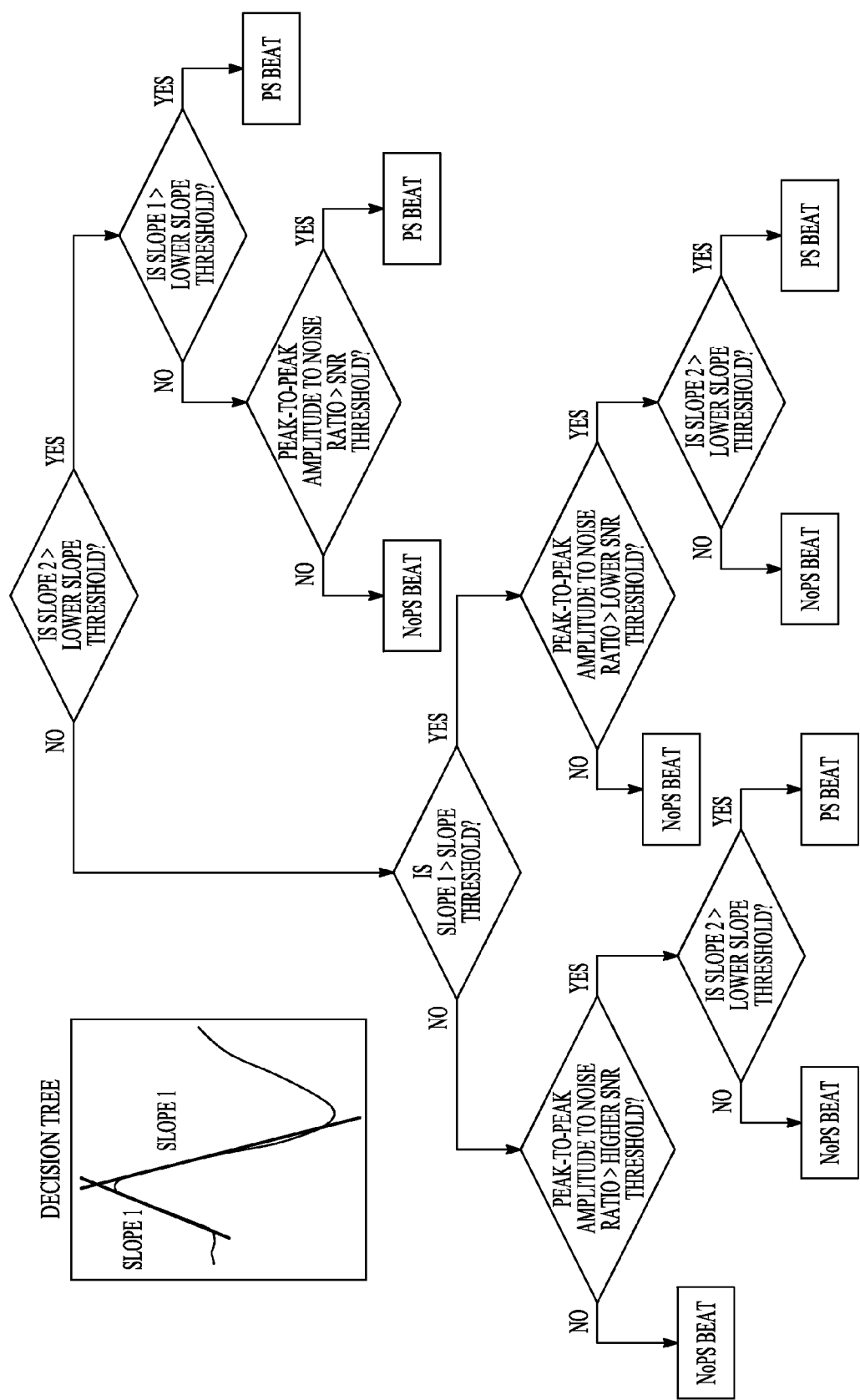
FIG. 18 illustrates, by way of example, an embodiment of a procedure for using a decision tree for analyzing morphological features of the beat signal to discriminate between PS beats and no PS beats.

FIG. 18 illustrates, by way of example, an embodiment of a procedure for using a decision tree for analyzing morphological features of the beat signal to discriminate between PS beats and NoPS beats. The decision tree presents a series of questions about the beat signal that can be answered yes or no. The answer to a particular question may lead to another question or to the determination for the beat signal (e.g. PS beat or NoPS beat). Logically, the questions in the tree may be arranged in a number of different ways to achieve the desired discrimination. Also, the analyzed parameters may vary. For example, FIG. 18 has been organized to analyze at the rising slope leading to the maximum peak and the falling slope leading away from the maximum peak, and to also analyze the peak-to-peak amplitudes against signal-to-noise thresholds. It is possible to analyze the peak-to-peak amplitudes against signal-to-noise thresholds before analyzing the slopes. Furthermore, it is possible to analyze the extrema values and timing between extrema using a number of decision points in the tree instead of or in addition to analyzing slopes. Therefore, the illustrated decision tree is but one example of how a decision tree can be logically arranged to discriminate between PS and NoPS beats.

Figure 19:
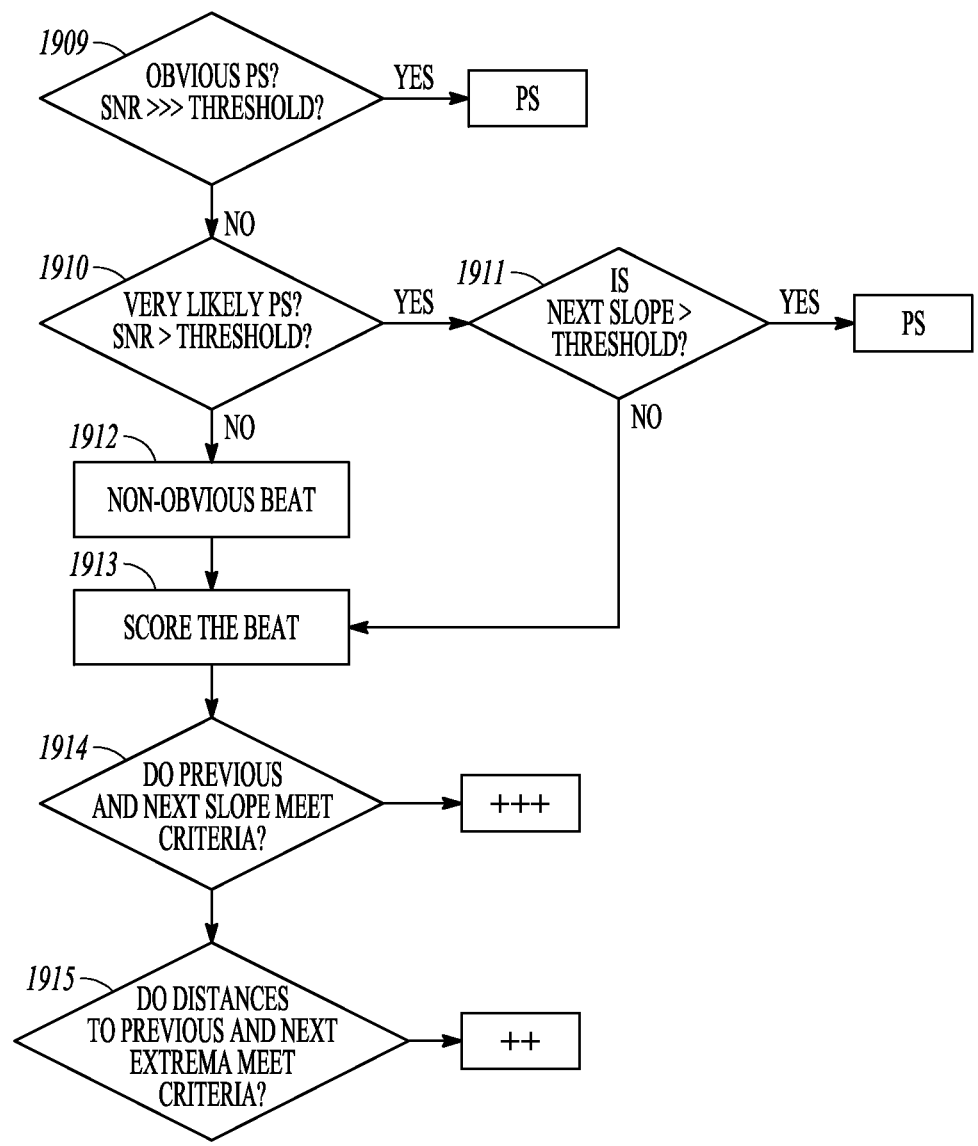
FIG. 19 illustrates, by way of example, an embodiment of a procedure for discriminating PS beats using both a decision tree for analyzing morphological features of the beat signal and scoring sensed parameters for specific morphological features.

FIG. 19 illustrates, by way of example, an embodiment of a procedure for discriminating PS beats using both a decision tree for analyzing morphological features of the beat signal and scoring sensed parameters for specific morphological features. For example, a first question in the decision tree may be crafted to identify the beat signals that are clearly PS beats 1909. A PS beat may be clearly identifiable based on a signal-to-noise ratio or based on other criteria that can be quickly determined with relatively little processing. If the beat signal cannot be identified as clearly a PS beat, then it can be determined if the beat signal is likely a PS beat 1910. This also may be determined based on a signal-to-noise ratio or on other criteria that can be quickly determined with relatively little processing. If the beat signal is determined to likely be a PS beat, then the PS beat can be confirmed with another decision tree question 1911 (e.g. Is the next slope greater than a threshold?). If the PS beat cannot be confirmed at 1911, then the morphological feature(s) of the beat signal can be scored at 1913. If the beat signal cannot be determined to likely be a PS beat at 1910, then the beat signal is a non-obvious beat signal 1912, and the morphological feature(s) of the beat signal can be scored at 1913. The scoring may use weighted scoring of multiple morphological features, such as scoring based on slope 1914, based on distances between extrema 1915, and/or based on other morphological features of the beat signal.

Scoring-Correlation Combination

Some embodiments of the present subject matter may be configured to detect the presence and threshold of phrenic nerve stimulation based on a combination approach using both a correlation between the PS sensor signal and a template, and morphological feature-based score of the PS sensor signal which may use a feature score and/or decision tree. When triggered, a template library may be generated based on the beat signal. As the beat signal is read, it can be determined if the beat signal matches a previous beat-type template in the library. This matching decision is based on the correlation between the current beat and the beat-template. If the beat does not match any template already stored in the library, and there is still room to store more templates, the current beat's template is scored with the morphological feature algorithm. This score determines whether to annotate the template as PS or NoPS. The annotated template will then be added to the library. If the beat does match a template that is already stored, the annotation of that template will determine if the current beat is a PS beat or NoPS beat.

In some embodiments, the algorithm may also assess whether or not a beat is a PS beat or a NoPS beat, at any time with any template. The template may be a template generated by the library method discussed above, or, it could be from some other method (physician input, patient input, a population-based pre-programmed template, etc.). Some embodiments may generate templates from the beat signal in parallel with scoring features of the beat signal. If the score is high enough, the beat may be quickly labeled as a PS beat. If the score is too low, the beat may be labeled a NoPS beat. If the score is somewhere in the middle however, the correlation of the beat with the stored PS template may be assessed to determine that the beat signal is a PS beat if it correlates with the PS template, or determine that the beat signal is a NoPS beat if it does not correlate with the PS template. Thus, with the use of the scoring method to quickly categorize the beat signal, fewer beat signals are correlated to a template which reduces the overall processing to discriminate between PS beats and NoPS beats.

Many different types of PS and No PS templates can be generated and stored. According to various embodiments, template libraries may be created to only store PS beat templates, or to only store NoPS beat templates, or to store both PS beat templates and NoPS beat templates.

The systems and devices may be configured to trigger the procedures to classify beats using a variety of triggers. For example, the system or device may be commanded in-clinic or by an ambulatory patient to begin a procedure to classify the beats. A characteristic of the PS sensor signal may trigger the procedure. For example, if the amplitude of the signal is larger than a predetermined value, then the system or device may be triggered to classify the beats. Some embodiments continuously classify beats in an ambulatory setting. The beat classification may be triggered with a pacing threshold test. Score here, as in advanced template generation, is a general term to refer to the output of the morphological feature-based algorithm. The score may be the score result from the scoring version, or could be a level of confidence associated with the number of tree branches accessed. By including the correlation step with the result of the morphological feature-based algorithm, the feature-based algorithm can be more sensitive to PS beats without the worry of false-positive detections or false-negatives.

Figure 20:
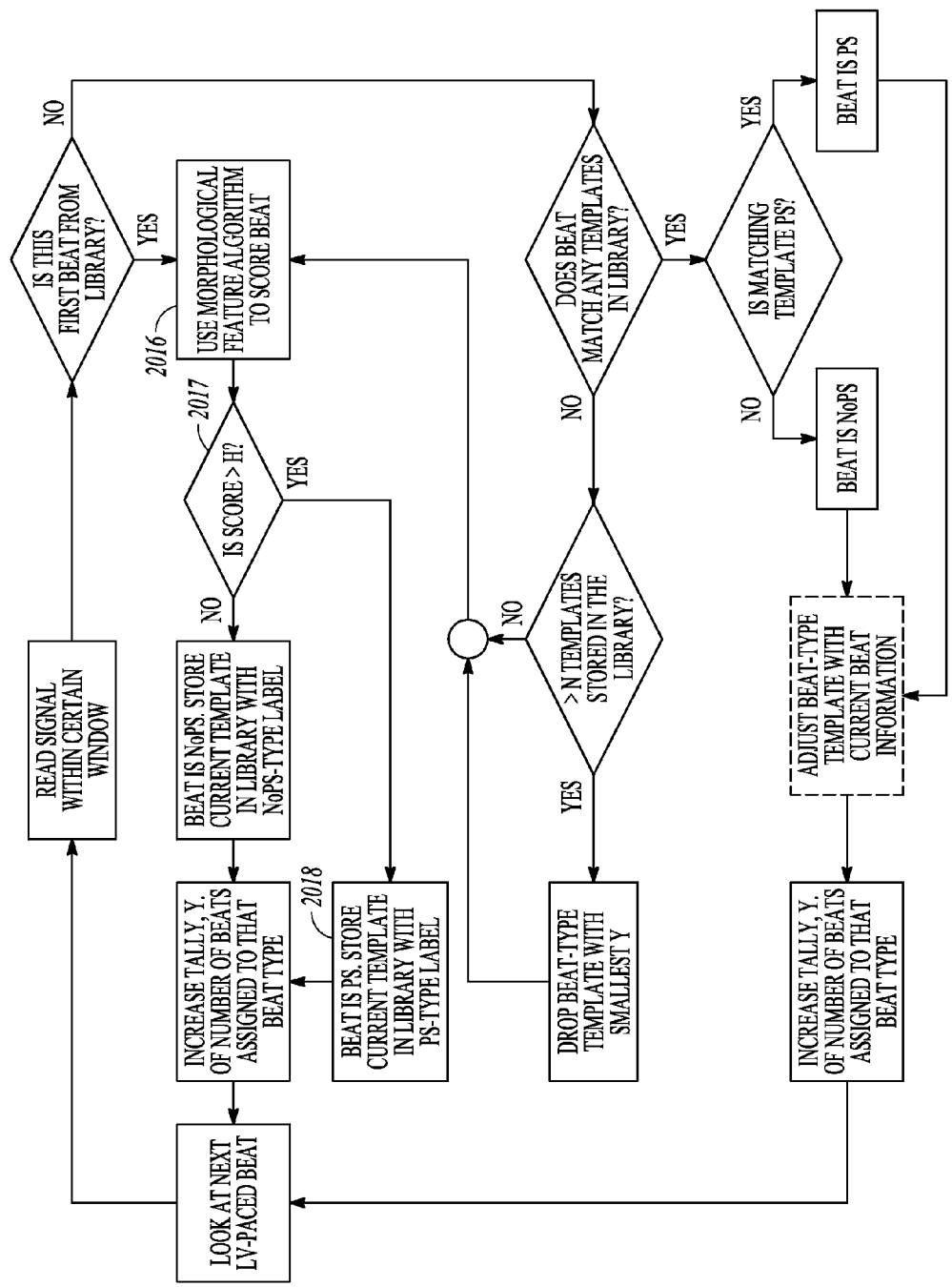
FIG. 20 illustrates, by way of example, an embodiment of a procedure for discriminating PS beats that uses correlation to create templates in a library and to score the beat signals to quickly identify the beat-type templates that can be labeled as a PS template.

FIG. 20 illustrates, by way of example, an embodiment of a procedure for discriminating PS beats that uses correlation to create templates in a library and to score the beat signals to quickly identify the beat-type templates that can be labeled as a PS template. FIG. 20 has similarities to FIG. 12, which was described in detail above and need not be repeated here. However, differences between FIG. 20 and FIG. 12 are illustrated at 2016, 2017, and 2018. If a beat signal does not match an existing beat-type template, either because it is a new beat signal for a library without beat-type templates or because the beat signal does not match the beat-type templates stored in the library, the morphological feature(s) of the beat signal can be scored at 2016. The score may be a weighted score of the features. The score can be compared to a defined score threshold at 2017. If the score is high enough, for example, the beat signal can quickly be classified as a PS template at 2018 with a high degree of confidence, and beat signal can be classified as and declared a PS beat.

Figure 21:
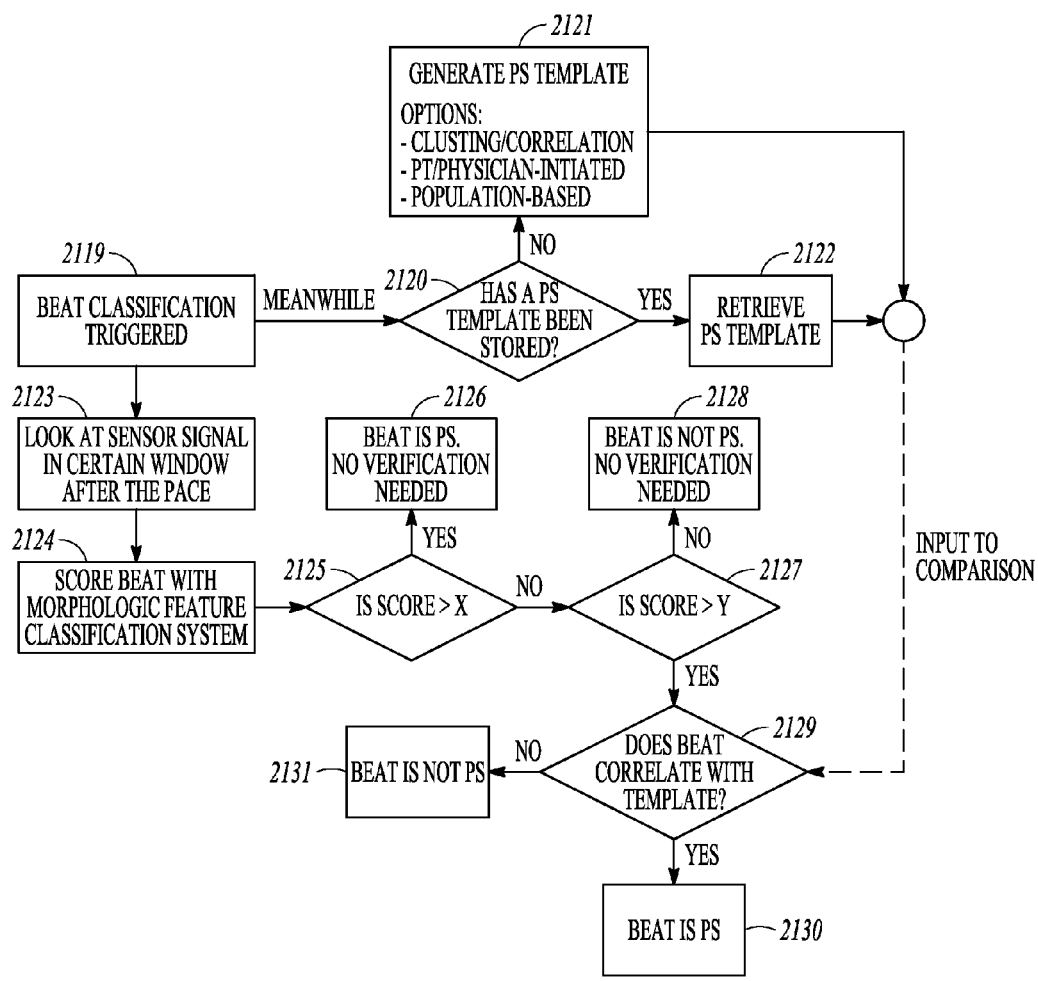
FIG. 21 illustrates, by way of example, an embodiment of a procedure for discriminating PS beats that scores morphological features of the beat signals to quickly identify some beat signals as PS beats or NoPS beats, and that correlates the remainder of the beat signals to a PS template to discriminate between PS beats and NoPS beats.

FIG. 21 illustrates, by way of example, an embodiment of a procedure for discriminating PS beats that scores morphological features of the beat signals to quickly identify some beat signals as PS beats or NoPS beats, and that correlates the remainder of the beat signals to a PS template to discriminate between PS beats and NoPS beats. In the illustrated embodiment, once a beat classification procedure has been triggered 2119, the procedure may determine if a PS template is stored in the system 2120. If it is not stored in the system, the PS template is obtained 2121. The PS template may be created in some embodiments, or may be input by a patient or physician. The PS template may be patient specific or based on a population of patients. If the PS template is already stored, the PS template is retrieved 2122 for a correlation procedure. In parallel, the beat signal in the window of time after the pace is analyzed 2123, and the morphological features of the beat signal are scored 2124. The score can be compared to a first value 2125 to determine if the beat signal is clearly a PS beat requiring no further verification 2126, and can be compared to a second value 2127 to determine if the beat signal is clearly a NoPS beat requiring no further verification 2128. If the scoring algorithm is unable to identify the beat signal as clearly either a PS beat or a NoPS beat, then the beat signal can be correlated with the PS template 2129 to determine if the beat signal is a PS beat 2130 or a NoPS beat 2131.

In an example of a method for detecting PS beats, the method may include pacing a heart with cardiac paces, sensing a physiological signal for use in detecting PS beats where sensing the physiological signal includes sensing beat signals from a window of time defined based on cardiac pace times, building a library of beat-type templates including storing beat signal data for the sensed beat signals in beat-type templates, and using the PS template to detect PS beats. Storing beat signal data may include determining if the beat signal data for a currently-analyzed beat signal matches an existing beat-type template in the library, and creating a new beat-type template if there is no match or increasing a tally for the beat-type template if there is a match, and declaring that one of the beat-type templates to be a PS template when the tally for one of the beat-type templates reaches a defined threshold.

In an example of a method for detecting PS beats, the method may include pacing a heart with cardiac paces, sensing a physiological signal for use in detecting PS beats where sensing the physiological signal includes sensing beat signals from a window of time defined based on cardiac pace times, identifying morphological features for a sensed beat signal, and using the identified morphological features to determine if the sensed beat signal is a PS beat. Using the identified morphological features to determine if the sensed beat signal is a PS beat may include using weight-based scoring of the identified morphological features to analyze the identified morphological features. Using the identified morphological features to determine if the sensed beat signal is a PS beat may include using a decision tree to analyze the identified morphological features.

In an example of a method for detecting PS beats, the method may include pacing a heart with cardiac paces, sensing a physiological signal for use in detecting PS beats where sensing the physiological signal includes sensing beat signals from a window of time defined based on cardiac pace times, building a library of beat-type templates including storing beat signal data for the sensed beat signals in beat-type templates. Storing beat signal data may include determining if beat signal data for a currently-analyzed beat signal matches an existing beat-type template in the library, scoring the beat signal data for the sensed beat signals and creating a score-generated PS template from the beat signal data if there is no match to an existing beat-type template and if the score favorably compares to a defined threshold for the score, creating a new beat-type template if there is no match and the score does not favorably compare to the defined threshold for the score, and increasing a tally for the beat-type template if there is a match and declaring the beat type template to be a clustering-generated PS template when the tally reaches a defined tally threshold. The method may further include detecting PS beats using the score-generated PS template or the clustering-generated PS template.

In an example of a method for detecting PS beats, the method may include pacing a heart with cardiac paces, sensing a physiological signal for use in detecting PS beats where sensing the physiological signal includes sensing beat signals from a window of time defined based on cardiac pace times, scoring morphological features of the sensed beat signals, using the score to identify those sensed beat signals that can be declared PS beats with a high degree of confidence and those sensed beat signals that can be declared NoPS beats with a high degree of confidence, and correlating sensed beats that cannot be declared, with a high degree of confidence, as either PS beats or NoPS beats to a PS template, and declaring the sensed beats that are correlated with the PS template to be PS beats.

In an example, a system includes a cardiac pulse generator configured to generate cardiac paces to pace the heart, a sensor configured to sense a physiological signal for use in detecting pace-induced phrenic nerve stimulation where the pace-induced phrenic nerve stimulation is phrenic nerve stimulation induced by electrical cardiac pace signals, and a phrenic nerve stimulation detector configured to analyze the sensed physiological signal to detect PS beats where the PS beats are cardiac paces that induce phrenic nerve stimulation. The phrenic nerve stimulation detector may be configured to correlate signal data for sensed beat signals to a PS template to detect PS beats, or may be configured to analyze morphological features of sensed beat signals to detect PS beats, or may be configured to detect PS beats using a combination that both correlates signal data for sensed beat signals to a PS template and analyzes morphological features of sensed beat signals.

PS Stimulation Threshold Determination

Some embodiments of the present subject matter may be configured to detect the presence and threshold of phrenic nerve stimulation (PS) using a step-up test or step-down test or a combination of the step-up and step-down tests. The PS threshold may be determined alone or in conjunction with a pace capture threshold test (e.g. an LV threshold test). An LV threshold test often is a step-down test that initially uses a high energy pace to confirm capture of the myocardium and that steps down the pacing energy to determine the lowest pacing energy level that still paces the heart. The PS threshold tests may either adjust the pacing amplitude or pulse width to determine the PS threshold. A pacing output level refers to a pacing energy level that may be based on an amplitude of the paces and/or a pulse width of the paces. In addition, the PS threshold may be determined using a combination of step-up and step-down tests. The step sizes may be predefined, or may be dynamically adjusted based on the observed results during the test.

In a step-up test, the pacing voltage may be increased by predefined intervals until PS is observed over several beats or with a high response amplitude. If there is not high confidence that PS has been detected, a PS confirmation step may be conducted. The pacing output may be increased for several cardiac cycles, increasing the likelihood of stimulating the phrenic nerve, to determine if the same PS characteristics are observed. Alternatively or additionally, the pacing output may be decreased to determine the characteristics of NoPS beats for comparison.

In a step-down test, the pacing voltage may be decreased by pre-determined intervals until PS is no longer observed over several beats. Alternatively, the pacing output decrease may be adaptively adjusted based on the amplitude of PS response. For instance, a larger pacing output decrease could be employed when a large PS amplitude and high PS frequency are observed.

According to some embodiments, the pacing parameters are adaptively adjusted during a test based on the patient's PS response to quickly and accurately measure PS threshold. For example, some embodiments adjust pacing amplitude output, or pulse width output, or the number of paces at a level, or a combination thereof. Thus, the test can be implemented to determine an appropriate characteristic of a myocardial pace (e.g. an appropriate amplitude and/or pulse width) that avoids PS.

The pacing output can be adaptively adjusted based on the PS response. A larger pacing output drop could be used when a higher PS amplitude to baseline ratio or higher frequency is observed. When PS amplitude from multiple steps are observed, a linear or polynomial or other functions may be fitted over the PS response to adjust the pacing output subsequently. A step-up process may be initiated when PS response disappears after the output adjustment.

Figure 22:
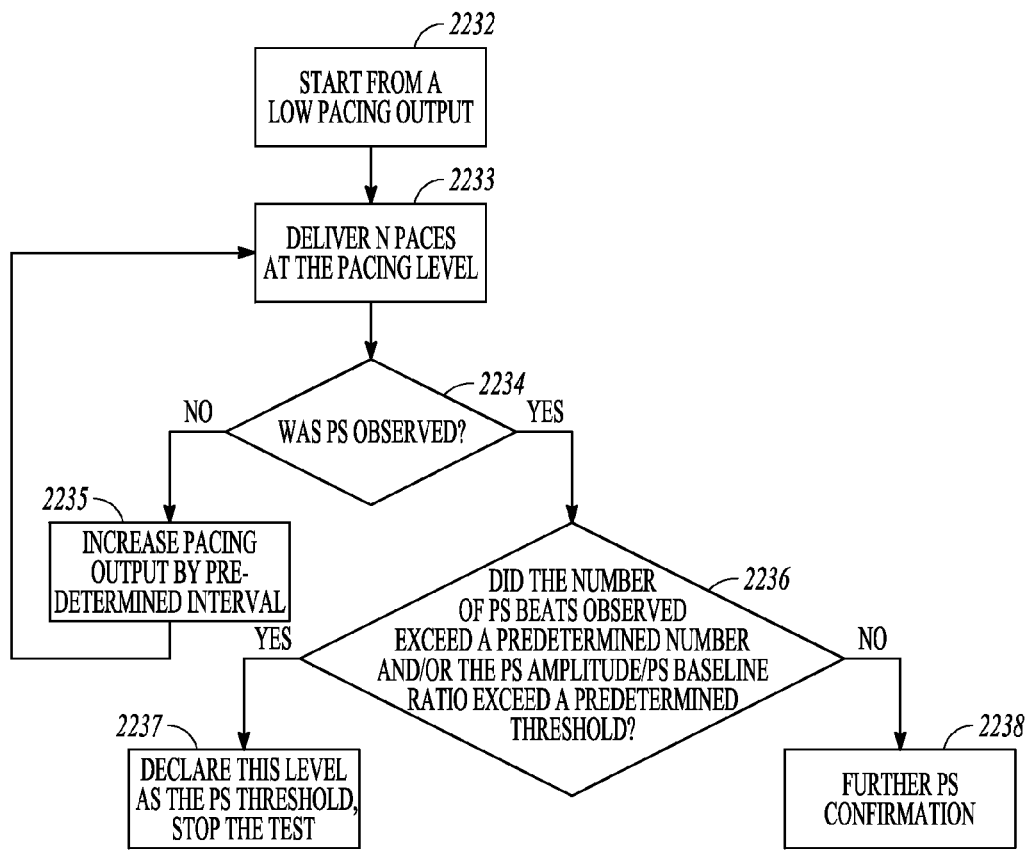
FIG. 22 illustrates, by way of example, an embodiment of a step-up procedure for determining a PS threshold.

FIG. 22 illustrates, by way of example, an embodiment of a step-up procedure for determining a PS threshold. The illustrated procedure may be used as a standalone process for determining PS threshold or in conjunction with an LV step-up threshold test. When used as a standalone test, the procedure may use coarser steps. When used with an LV step-up threshold test, finer step intervals are used, and beat signals from multiple consecutive levels can be used.

The illustrated step-up procedure is initiated with a relatively low pacing output 2232, and a defined number of paces are delivered at the pacing level 2233. The beat signals are analyzed to determine if PS beats were observed at the pacing level 2234. If no PS beats were observed, the pacing output is increased to a higher pacing output level 2235. If PS beats were observed, then the observed PS beats or characteristics thereof may be compared to one or more thresholds at 2236. For example, the number of PS beats that were observed at the level may be compared to a threshold number. In another example, a ratio of the amplitude of the observed PS beat(s) to the baseline level may be compared to a threshold. The pacing level may be declared to be the PS threshold 2237 based on the comparison, or further PS confirmation may be performed 2238. The threshold or thresholds may be set based on physician preference. Furthermore, the procedure may differ depending on whether the test is performed in a clinical setting or in an ambulatory setting. For example, clinical settings may not require the PS confirmation.

Figure 23:
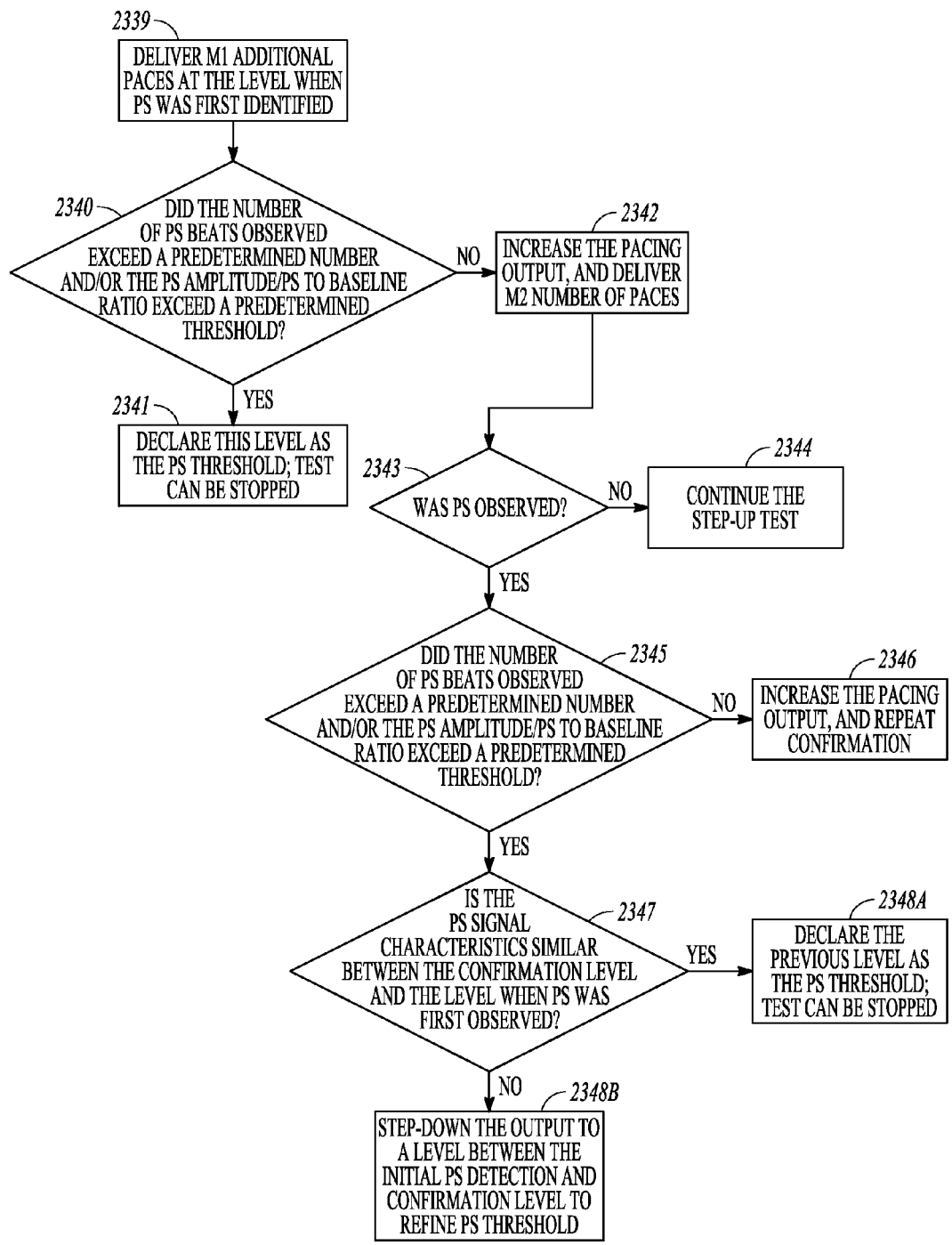
FIG. 23 illustrates, by way of example, an embodiment of a procedure for confirming a PS threshold by increasing the pacing output level.

FIG. 23 illustrates, by way of example, an embodiment of a procedure for confirming a PS threshold by increasing the pacing output level. If some beat signals appear to be PS beats for a pacing level from FIG. 22, then the illustrated procedure delivers additional paces at the same pacing level 2339. If PS beats were observed, then the observed PS beats or characteristics thereof may be compared to one or more thresholds at 2340. For example, the number of PS beats that were observed at the pacing output level may be compared to another threshold number different from the threshold used at 2236 in FIG. 22. In another example, a ratio of the amplitude of the observed PS beat(s) to the baseline level may be compared to another threshold different from the threshold used at 2236 in FIG. 22. If the comparison is favorable, then the pacing level can be declared to be the PS threshold and the test can be stopped 2341. Otherwise, the procedure increases pacing output level and delivers an additional number of paces 2342. The increase in the pacing output may depend on the frequency and/or the amplitude of the observed PS beats. For example, the increase interval may be less for larger PS beat amplitudes or if more PS beats were observed as the current pacing output level is close to the PS threshold. Coarser steps may be used. Some embodiments may use fixed intervals to adjust the pacing output levels. If PS beats are not observed 2343, then the step-up test continues at 2344 in the illustrated embodiment. If PS beats are observed 2343, then the observed PS beats or characteristics thereof may be compared to one or more thresholds at 2345. For example, the number of PS beats that were observed at the level may be compared to another threshold number different from the thresholds used at 2236 in FIG. 22 or 2340. In another example, a ratio of the amplitude of the observed PS beat(s) to the baseline level may be compared to another threshold different from the thresholds used at 2236 in FIG. 22 or 2340. If the comparison is not favorable at 2345, the pacing output level can be increased and the confirmation can be repeated 2346. If the comparison is favorable at 2345, then some embodiments may further compare the signal characteristics between the confirmation level and the level where PS beats were first observed for similarities 2347, and declare the previous level as the PS threshold 2348A if there are similarities. If there are not similarities found in the comparison performed at 2347, the output level can be stepped-down to a level between the level at which the PS beats were first observed and the confirmation level to further refine the PS threshold, and the confirmation can be repeated 2348B.

Figure 24:
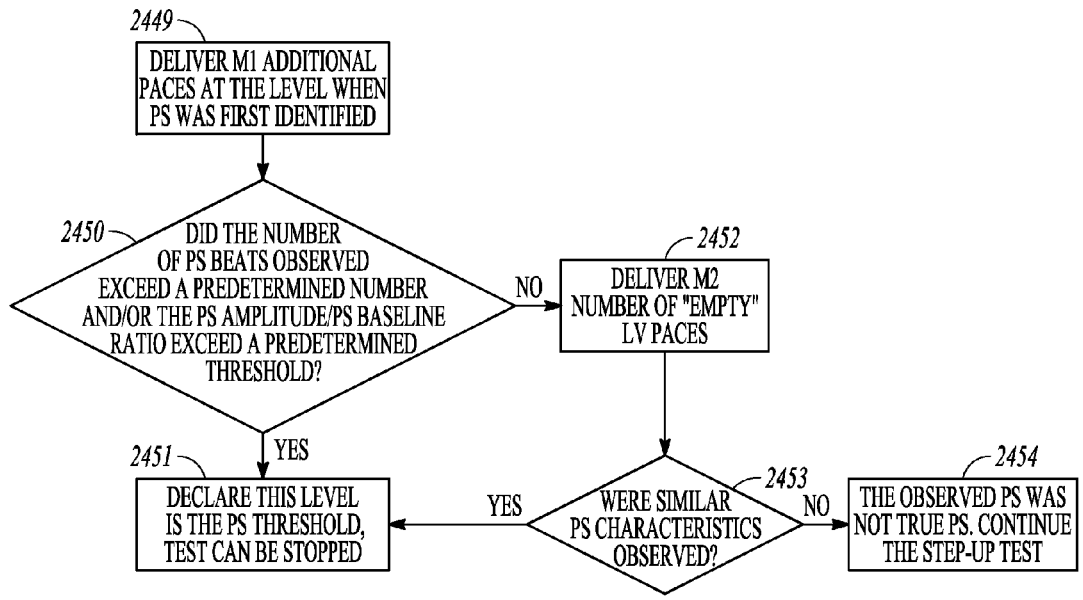
FIG. 24 illustrates, by way of example, an embodiment of a procedure for confirming a PS threshold by reducing the pacing output level.

FIG. 24 illustrates, by way of example, an embodiment of a procedure for confirming a PS threshold by reducing the pacing output level. If some beat signals appear to be PS beats for a pacing level from FIG. 22, then the illustrated procedure delivers additional paces at the same pacing level 2449. If PS beats were observed, then the observed PS beats or characteristics thereof may be compared to one or more thresholds at 2450. For example, the number of PS beats that were observed at the level may be compared to a second threshold number different from the threshold used at 2236 in FIG. 22. In another example, a ratio of the amplitude of the observed PS beat(s) to the baseline level may be compared to a second threshold different from the threshold used at 2236 in FIG. 22. If the comparison is favorable, then the pacing level can be declared to be the PS threshold and the test can be stopped 2451. If the comparison is not favorable, then a defined number of "empty" paces are delivered at 2452 in an attempt to see if similar PS beat signatures were observed. Empty paces can be delivered by reducing an LV pacing output to a very low value, such as 0.1 V, or by delivering RV pace and analyzing the signals based on the RV-LV offset. If similar PS beat characteristics are not observed at 2453, then the level can be declared to be the PS threshold and the test can be stopped at 2451. The "empty" pace should still provide the same cardiac components, which allow for a meaningful comparison. The pacing level for an empty pace may be adjusted to a level that has LV capture but does not have PS. If similar PS beat characteristics are observed at 2453, then the step-up test in FIG. 22 continues as indicated at 2454.

Figure 25:
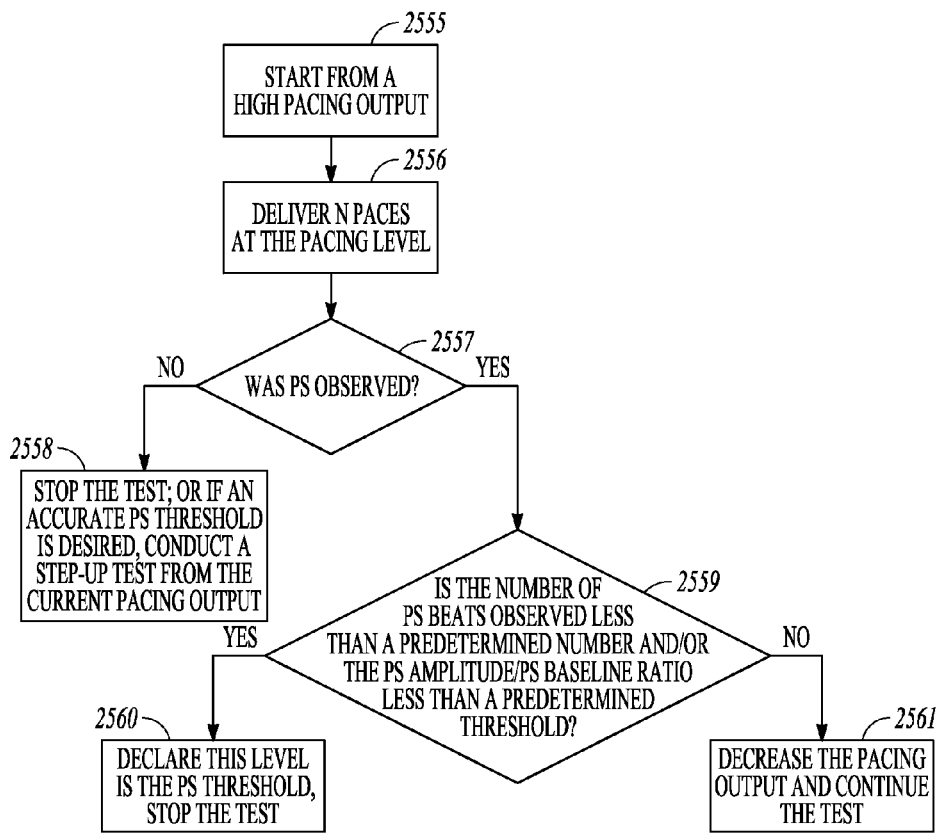
FIG. 25 illustrates, by way of example, an embodiment of a step-down procedure for determining a PS threshold.

FIG. 25 illustrates, by way of example, an embodiment of a step-down procedure for determining a PS threshold. The illustrated procedure may be used as a standalone process for determining PS threshold or in conjunction with an LV step-up threshold test. When used as a standalone test, the procedure may use coarser steps. When used with an LV step-up threshold test, finer step intervals are used, and beat signals from multiple consecutive levels can be used.

A procedure is initiated with a relatively high pacing output 2555, and a defined number of paces are delivered at the pacing level 2556. The beat signals are analyzed to determine if PS beats were observed at the pacing level 2557. The analysis of the beat signals may include a procedure disclosed. If no PS beats were observed, then the test can be stopped or a step-up test may be initiated from the current pacing output 2558. If PS beats were observed, then the observed PS beats or characteristics thereof may be compared to one or more thresholds at 2559. For example, the number of PS beats that were observed at the level may be compared to a threshold number. In another example, a ratio of the amplitude of the observed PS beat(s) to the baseline level may be compared to a threshold. The pacing level may be declared to be the PS threshold 2560 based on the comparison. If the comparison is not favorable, the pacing output can be decreased at 2561 and the test can continue at 2556. The pacing output decrease may be performed adaptively based on the PS beats using, by way of example, the amplitude of the PS beats, the ratio of the amplitude of the PS beats to the baseline level, the frequency of PS beats, or various combinations thereof. The threshold may be set based on physician preference. Furthermore, the procedure may differ depending on whether the test is performed in a clinical setting or in an ambulatory setting.

In an example of a method, the method includes testing for the phrenic nerve stimulation (PS) threshold. If PS beats are detected at the pacing output level, the detected PS beats may be analyzed using criteria to determine if the pacing output level can be declared to be the PS threshold. If the pacing output level cannot be declared to be the PS threshold based on the analysis of the PS beat at the pacing output level, a PS beat confirmation procedure may be performed. The PS beat confirmation procedure may include delivering additional cardiac paces at the pacing output level to generate additional PS beats, and analyzing the detected PS beats using other criteria to determine if the pacing output level can be confirmed as the PS threshold.

In an example, a system includes a cardiac pulse generator configured to generate cardiac paces to pace the heart, a sensor configured to sense a physiological signal for use in detecting pace-induced phrenic nerve stimulation, a phrenic nerve stimulation detector configured to analyze the sensed physiological signal to detect PS beats, and a controller configured to test for phrenic nerve stimulation (PS) threshold. The controller may be configured to control the cardiac pulse generator to deliver cardiac paces at a pacing output level, use the phrenic nerve stimulation detector to detect if the pacing output level causes PS beats, analyze the detected PS beats if PS beats are detected at the pacing output level, and perform a PS beat confirmation procedure if the pacing output level cannot be declared to be the PS threshold based on the analysis of the PS beat at the pacing output level. To analyze the detected PS beats, the controller may use criteria to determine if the pacing output level can be declared to be the PS threshold. The PS beat confirmation procedure may include delivering additional cardiac paces at the pacing output level to generate additional PS beats, and analyzing the detected PS beats using other criteria to determine if the pacing output level can be confirmed as the PS threshold. The system may include at least one implantable medical device that includes the cardiac pulse generator, the sensor, the phrenic nerve stimulation detector and the controller. The system may include at least one implantable medical device and at least one external device, where the implantable medical device(s) include the cardiac pulse generator, and the external device(s) including the phrenic nerve stimulation detector. One of ordinary skill in the art will understand that, the modules and other circuitry shown and described herein can be implemented using software, hardware, firmware and combinations thereof.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a sequence of instructions which, when executed by one or more processors, cause the processor(s) to perform the respective method. In various embodiments, the methods are implemented as a set of instructions contained on a computer-accessible medium such as a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for detecting PS beats, wherein the PS beats are cardiac paces that induce phrenic nerve stimulation, the method comprising:
   pacing a heart with cardiac paces;
   sensing a physiological signal for use in detecting PS beats, wherein sensing the physiological signal includes sensing beat signals from a window of time defined based on cardiac pace times;
   identifying morphological features for a sensed beat signal; and
   using the identified morphological features to determine if the sensed beat signal is a PS beat, wherein using the identified morphological features to determine if the sensed beat signal is a PS beat includes at least one of:
      analyzing the identified morphological features using weight-based scoring of the identified morphological features, wherein weight-based scoring weights some morphological features differently when determining if the sensed beat signal is the PS beat; or
      analyzing the identified morphological features using a decision tree to determine if the sensed beat signal is the PS beat.

2. The method of claim 1, wherein using the identified morphological features to determine if the sensed beat signal is a PS beat includes using the weight-based scoring of the identified morphological features to analyze the identified morphological features.

3. The method of claim 2, wherein the morphological features include features selected from the group of features consisting of: peak timing; amplitude; peak-to-peak amplitude; slope leading to peak; slope leading away from peak, timing and amplitude of surrounding extrema, area under signal, and signal frequency components.

4. The method of claim 2, further comprising identifying noisy beat signals and removing noisy beat signals from use in the weight-based scoring of the identified morphological features.

5. The method of claim 1, wherein using the identified morphological features to determine if the sensed beat signal is a PS beat includes using the decision tree to analyze the identified morphological features.

6. The method of claim 1, wherein using the identified morphological features to determine if the sensed beat signal is a PS beat includes using a combination of the weight-based scoring of the identified morphological features and the decision tree to analyze the identified morphological features.

7. The method of claim 6, wherein using the combination includes identifying if the determination has a high degree of confidence using at least one decision point within the decision tree to quickly declare that the sensed beat signal is a PS beat or a NoPS beat with the high degree of confidence.

8. The method of claim 7, wherein using the combination further includes scoring the morphological features if unable to quickly declare that the sensed beat signal is a PS beat or is a NoPS beat.

9. The method of claim 8, wherein using the combination further includes using at least one additional decision point in the tree if the scored morphological features are unable to declare with a high degree of confidence that the beat signal is the PS beat or a NoPS beat.

10. A method for detecting PS beats, wherein the PS beats are cardiac paces that induce phrenic nerve stimulation, the method comprising:
    pacing a heart with cardiac paces;
    sensing a physiological signal for use in detecting PS beats, wherein sensing the physiological signal includes sensing beat signals from a window of time defined based on cardiac pace times;
    scoring morphological features of the sensed beat signals;
    using the score to identify those sensed beat signals that can be declared PS beats with a high degree of confidence and those sensed beat signals that can be declared NoPS beats with a high degree of confidence, and to identify those sensed beats that cannot be declared with the high degree of confidence as either a PS beat or a NoPS beat; and
    correlating those sensed beats that cannot be declared with a high degree of confidence to a PS template, and declaring the sensed beats that are correlated with the PS template to be a PS beat.

11. A system, comprising:
    a cardiac pulse generator configured to generate cardiac paces to pace the heart;
    a sensor configured to sense a physiological signal for use in detecting pace-induced phrenic nerve stimulation, wherein the pace-induced phrenic nerve stimulation is phrenic nerve stimulation induced by electrical cardiac pace signals;
    a phrenic nerve stimulation detector configured to analyze the sensed physiological signal to detect PS beats, wherein the PS beats are cardiac paces that induce phrenic nerve stimulation, wherein:
        the phrenic nerve stimulation detector is configured to correlate signal data for sensed beat signals to a PS template to detect PS beats; or
        the phrenic nerve stimulation detector is configured to analyze morphological features of sensed beat signals to detect PS beats, including weight some morphological features differently to detect PS beats or use a decision tree to analyze the identified morphological features to detect PS beats; or the phrenic nerve stimulation detector is configured to detect PS beats using a combination that both correlates signal data for sensed beat signals to a PS template and analyzes morphological features of sensed beat signals.

12. The system of claim 11, wherein the phrenic nerve stimulation detector is configured to correlate signal data for sensed beat signals to a PS template to detect PS beats, and is configured to build a library of beat-type templates, wherein in building the library the phrenic nerve stimulation detector is configured to:

determine if beat signal data for a currently-analyzed beat signal matches an existing beat-type template in the library, and create a new beat-type template if there is no match or increasing a tally for the beat-type template if there is a match; and declare that one of the beat type templates to be a PS template when the tally for one of the beat-type templates reaches a defined threshold.

13. The system of claim 11, wherein the phrenic nerve stimulation detector is configured to weight some morphological features differently to detect PS beats.

14. The system of claim 13, wherein the morphological features include features selected from the group of features consisting of: peak timing; amplitude; peak-to-peak amplitude; slope leading to peak; slope leading away from peak, timing and amplitude of surrounding extrema, area under signal, and signal frequency components.

15. The system of claim 13, in analyzing morphological features the phrenic nerve detector is configured to indentify noisy beat signals and remove noisy beat signals from use in the weight-based scoring of the identified morphological features.

16. The system of claim 11, wherein the phrenic nerve stimulation detector is configured to use a decision tree to analyze the identified morphological features to detect PS beats.

17. The system of claim 11, wherein the phrenic nerve stimulation detector is configured to analyze morphological features of sensed beat signals to detect PS beats, wherein in analyzing morphological features the phrenic nerve detector is configured to use a combination of weighting some morphological features different and using a decision tree to analyze the identified morphological features to detect PS beats.

18. The system of claim 11, wherein the phrenic nerve stimulation detector is configured to detect PS beats using a combination that both correlates signal data for sensed beat signals to a PS template and analyzes morphological features of sensed beat signals.

19. The system of claim 18, wherein the phrenic nerve stimulation detector is configured to store beat signal data for the sensed beat signals in beat-type templates within a library, wherein the phrenic nerve stimulation detector is configured to:

determine if beat signal data for a currently-analyzed beat signal matches an existing beat-type template in the library;

score the beat signal data for the sensed beat signals when there is no match;

create a score-generated PS template if the score favorably compares to a defined threshold for the score;

create a new beat-type template when there is no match and the score does not favorably compare to the defined threshold for the score;

increase a tally for the beat-type template when there is a match and declare the beat type template to be a clustering-generated PS template when the tally reaches a defined tally threshold; and detect PS beats using the score-generated PS template or the clustering-generated PS template.

20. The system of claim 18, wherein the phrenic nerve stimulation detector is configured to use the weight-based score to identify those sensed beat signals that can be declared PS beats with a high degree of confidence and those sensed beat signals that can be declared NoPS beats with a high degree of confidence, correlate sensed beats that cannot be declared with the high degree of confidence to a PS template, and declare the sensed beats that are correlated with the PS template to be PS beats.

* * * * *